United States Patent [19]

Jones et al.

[11] Patent Number: 5,236,927

[45] Date of Patent: Aug. 17, 1993

[54] ANTI-CANCER QUINAZOLINE DERIVATIVES

[75] Inventors: Terence R. Jones, La Jolla, Calif.; Ann L. Jackman; David R. Newell, both of Sutton, England

[73] Assignee: National Research Development Corporation, London, England

[21] Appl. No.: 625,695

[22] Filed: Dec. 12, 1990

Related U.S. Application Data

[63] Continuation of Ser. No. 425,345, Oct. 23, 1989, abandoned, which is a continuation of Ser. No. 165,369, Feb. 29, 1988, abandoned, which is a continuation of Ser. No. 867,568, May 28, 1986, abandoned.

[30] Foreign Application Priority Data

May 30, 1985 [GB] United Kingdom ............... 8513754

[51] Int. Cl.$^5$ ............... A61K 31/505; C07D 239/84
[52] U.S. Cl. .................... 514/259; 544/284; 544/285; 544/287; 544/289
[58] Field of Search ............... 544/284, 289; 514/259

[56] References Cited

U.S. PATENT DOCUMENTS

| | | | |
|---|---|---|---|
| 3,471,498 | 10/1969 | Davoll | 544/291 |
| 3,472,851 | 10/1969 | Davoll | 544/291 |
| 4,447,608 | 5/1984 | Jones et al. | 544/287 |
| 4,564,616 | 1/1986 | Jones et al. | 544/287 |
| 4,992,550 | 4/1989 | Hughes | 544/284 |

FOREIGN PATENT DOCUMENTS 031237A 7/1981 European Pat. Off.

OTHER PUBLICATIONS

Jones, et al., "Chemical Abstracts", vol. 106, 1987, col. 106:102679c. (Abstract of Eur. Pat. Appl. EP 204,529, Published Dec. 10, 1986).

Journal of the Chemical Society, 1953, Brown, "Some Pteridines related to Folic Acid . . . ".

Primary Examiner—C. Warren Ivy
Assistant Examiner—James H. Turnipseed
Attorney, Agent, or Firm—Nixon & Vanderhye

[57] ABSTRACT

A compound of formula I:

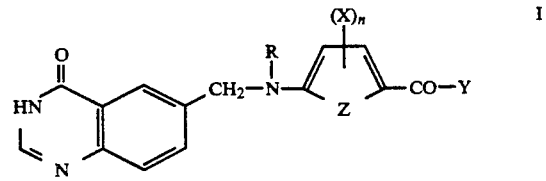

wherein R is hydrogen; or an alkyl, alkenyl or alkynyl group of up to 6 carbon atoms; n is 0; 1 or 2; Z represents —CH=CH— or —S—; each X independently represents halogeno, $C_1$-$C_4$ alkyl, $C_1$-$C_4$ alkoxy, nitro or trifluoromethyl; and Y represents a group of formula:

a) —NH—CH—COOH       (L-aspartic acid residue)
       |
       CH$_2$—COOH b) —NH—CH—COOH       (L-glutamic acid residue)
       |
       CH$_2$—CH$_2$—COOH or c) —NH—CH—COOH       (L-glutamyl-L-glutamic acid residue)
       |
       CH$_2$—CH$_2$—CO—NH—CH—COOH
                              |
                              CH$_2$—CH$_2$—CO—OH d) —NH—CH—CH$_3$       (L-alanine residue)
       |
       COOH or e) —NH—CH—CH$_2$—CH$_3$  (L-2-amino-butyric acid residue)
       |
       COOH or a pharmaceutically acceptable salt or ester thereof.

14 Claims, 6 Drawing Sheets

i) 2'-Fluoro CB 3804

Fig.7.

ANTI-CANCER QUINAZOLINE DERIVATIVES

This is a continuation of application Ser. No. 07/425,345, filed Oct. 23, 1989, now abandoned, which is a continuation of Ser. No. 07/165,369 filed 29 Feb. 1988 now abandoned, which is a continuation of Ser. No. 06/867,568 filed 28 May 1986, now abandoned.

THIS INVENTION relates to quinazoline derivatives which are potent anti-tumour (anti-cancer) agents.

The majority of the drugs which have been used to treat tumours have interfered either directly or indirectly with the replication of nucleic acids in the dividing cells. Many agents, termed antimetabolites, are designed to kill the tumour by depleting its essential growth elements in competing with and displacing the substrates of specific enzymes involved in DNA synthesis. Antimetabolites can be classified according to their specific inhibitory action and examples include analogues of purines and primidines and folic acid antagonists such as aminopterin and amethopterin (methotrexate).

Of the antimetabolites which are folic acid antagonists, methotrexate is used widely in the treatment of human malignant disease, particularly in the treatment of choriocarcinoma and osteosarcoma and in the maintenance therapy of acute lymphatic leukaemia. Its inhibition of the enzyme dihydrofolate reductase (DHRF, EC 1.5.1.4) causes a depletion of the one carbon-carrying tetrahydrofolate pools, resulting in the inhibition of the de novo synthesis both of thymine nucleotides and purine nucleotides necessary for DNA synthesis. Although the "purineless" state induced by methotrexate has been shown to cause toxicity to the gastro-intestinal tract of mice, it does not contribute to the cytotoxic effect of methotrexate against some cultured tumour cell lines and may antagonise it in others. Methotrexate does not require metabolic activation, and does not undergo significant metabolic degradation in the majority of cell types. Known causes of methotrexate resistance include reduced membrane transport and increased cellular DHFR. In this latter case the effective target of methotrexate may become thymidylate synthase (TS, EC 2.1.1.45), the enzyme catalysing the terminal step in the de novo synthesis of thymidylate required exclusively for DNA synthesis. Direct inhibition of TS may be achieved by an active metabolite of 5-fluorouracil, 5-fluorodeoxyuridine monophosphate. However, 5-fluorouracil resistance is frequently accompanied by a reduction in the appropriate activating enzymes and the drug may also have toxic effects which are attributable to its incorporation into RNA and DNA.

There is therefore a requirement for an agent which competes with the tetrahydrofolate cosubstrate of TS rather than the pyrimidine substrate, since such a compound may be expected to have activity equal or superior to methotrexate not only in methotrexate sensitive tumours, but also in those resistant by virtue of raised cellular DHFR. It should also be less toxic to the host since the synthesis of purines would not be affected. Further, folate analogues should be more effective than pyrimidines since they do not require metabolic activation.

Several classical quinazoline antifolates have been shown to be inhibitors of TS, e.g. 2-amino-4-hydroxy and 2,4-diamino derivatives, though while these latter have been shown to be reasonably effective inhibitors of TS they also bind extremely tightly to DHFR.

GB-2,065,653-B describes quinazolines of the formula A:

wherein
R represents:
1) a straight or branched chain unsaturated hydrocarbon group, or
2) a straight or branched chain saturated or unsaturated hydrocarbon group which is substituted by at least one heteroatom, the or each heteroatom being halogeno when R is a $C_1$ hydrocarbon group; or saturated carbocyclic group or group containing at least one heteroatom, the or each heteroatom being O, N or S when R contains a cyclic group;

n is 0 or an integer of 1–4;
X or, when n is an integer of at least 2, each X independently, represents a halogeno, $C_1$–$C_4$ alkyl, aryl or aralkyl group or a group including at least one heteroatom and Y represents a group of formula:

a)  (L-aspartate)

b)  (L-glutamate)

or c)

where $m \geq 1$ (poly-L-glutamates) or a pharmaceutically acceptable salt or ester thereof.

One of the more potent compounds of formula A which shows considerable promise in clinical use is N-(4-(N-((2-amino-4-hydroxy-6-quinazolyl)methyl)-prop-2-ynylamino)benzoyl)-L-glutamic acid also known as $N^{10}$-propargyl-5,8-dideazafolic acid and known under the code CB3717.

Analogues of 5,8-dideazafolic acid possessing various $N^{10}$ substituents of formula A have previously been shown to be good inhibitors of thymidylate synthase (TS), the terminal enzyme in the de novo thymidylate synthetic pathway.

The most potent of these, $N^{10}$-propargyl-5,8-dideazafolic acid (CB3717) was found to be active against L1210 cells grown either in vitro or in vivo. The cytotoxic effect of CB3717 was prevented in both cases by thymidine, the salvage precursor for thymidylate synthesis. This is consistent with inhibition of TS being rate-limiting in the oxidation-reduction cycle of tetrahydrofolate ($FH_4$) As with other 5,8-dideaza analogues of folic acid inhibition of dihydrofolate reductase (DHFR) is fairly potent in cell-free systems but both mathematical modelling and experimental evidence confirm that inhibition of DHFR is not the primary locus of action of this compound.

In both mouse and man toxicity is observed to the liver and kidney. The former toxicity is manifested as a transient rise in alanine transaminase accompanied by a feeling of "malaise" and the latter as a rise in plasma urea (mouse) or a fall in glomerular filtration rate (GFR)(man). Several minor and partial responses have been noted during the Phase I/II clinical studies (particularly breast and ovary). Thus CB3717 possesses antitumour properties in man but its use is hindered by the apparently non-dose-related (although not life-threatening) hepatic toxicity.

A role therefore exists for a second-generation antifolate that is devoid of such toxic side-effects whilst retaining the essential characteristics for good tumour inhibition. However, although poor solubility of CB3717 at acid pH most probably accounts for renal toxicity, no clue as to the cause of the hepatic toxicity has been forthcoming. Thus chemical synthesis, although rational in terms of seeking another potent TS inhibitor, has had to be empirical in the search for a non hepato-toxic compound.

We have now discovered a new class of analogues of 5,8-dideazafolic acid which retain valuable TS inhibitory properties but which exhibit reduced hepatic toxicity compared to that of CB3717 and related compounds of formula A.

Accordingly the present invention provides compounds of the general formula I:

wherein
R represents:
1) hydrogen or
2) a straight or branched chain saturated or unsaturated hydrocarbon group, or
3) a straight or branched chain saturated or unsaturated hydrocarbon group which is substituted by at least one heteroatom, the or each heteroatom being halogeno when R is a $C_1$ hydrocarbon group, by a saturated carbocyclic group or by a group containing at least one heteroatom, the or each heteroatom being 0, N or S when R contains a cyclic group;

n is 0, 1 or 2,

Z represents —CH═CH— or —O— or —S—;

X or, when n is an integer of at least 2, each X independently, represents a halogeno, $C_1$–$C_4$ alkyl, aryl or aralkyl group or a group including at least one heteroatom and Y represents a group of formula:

a) —NH—CH—COOH     (L-aspartic acid residue)
        |
        CH$_2$—COOH b) —NH—CH—COOH     (L-glutamic acid residue)
        |
        CH$_2$—CH$_2$—COOH or where m is $\geq 1$ (poly-L-glutamic acid residues);

d) —NH—CH—CH$_3$     (L-alanine residue)
        |
        COOH or e) —NH—CH—CH$_2$CH$_3$     (L-2-amino-butyric acid residue)
        |
        COOH or a pharmaceutically acceptable salt or ester thereof.

The compounds of the present invention are useful as anti-cancer agents which are either active as such or are suitable as pro-drugs which can be converted in vivo to provide active compounds.

Preferred substituents R as defined under 2) in formula I are straight or branched chains containing 2–6 e.g., 4 and particularly 2 or 3, carbon atoms and especially those having unsaturation at least in the 2- or in the ω-position. Examples of such groups are alkenyl, alkadienyl, alkynyl and alkadiynyl groups and particular examples are vinyl, allyl, propenyl, propargyl, but-2-ynyl, but-3-ynyl and 1-methylprop-2-ynyl. Examples of saturated groups R include methyl or ethyl.

Preferred groups R as defined under 3) in formula I are straight or branched chains containing up to 6 carbon atoms in the hydrocarbon chain, and particularly groups containing up to a total of 6, for instance up to a total of 3 carbon atoms in the group R as a whole. The saturated hydrocarbon chain preferably contains 1–3 carbon atoms while the unsaturated hydrocarbon chain preferably contains 2 or 3 carbon atoms. There are preferably 1 or 2 or 3 substituent groups on the chains. Suitable heteroatom substituents include halogeno, e.g. Cl or F, 0 and S, which can be attached to a carbon atom other than the α-carbon atom. Examples of such R groups are formyl, 1-oxoethyl, 1-oxopropyl, 2-oxopropyl, formylmethyl, acryloyl, propiolyl, 2,2,2-trifluoroethyl, 2-chloro- or 2-fluoroethyl, methoxymethyl and methylthiomethyl.

Preferred carbocyclic substituent groups contain 3–6 ring carbon atoms, particularly 3–5. The carbocyclic ring may itself have at least one $C_1$–$C_4$ alkyl substituent, preferably methyl, of which there are preferably 1–3, particularly 1.

The substituent groups containing at least one heteroatom referred to in definition 3) of R preferably contain 1–6, particularly 1–4, heteroatoms for example halogeno, 0, N or S. Particular examples of such groups are OH, NH$_2$, CONH$_2$, COOH and salts and esters thereof, CN, NO$_2$, SH, methylsulphonyloxy, alkoxy and amino acid radicals. Thus, the group R as defined under 3) may be, for example, hydroxyalkyl, such as 2-hydroxyethyl or 3-hydroxypropyl, carbamoylalkyl such as carbamoylmethyl, aminoalkyl such as 2-aminoethyl, mercaptoalkyl such as 2-mercaptoethyl, cyanoalkyl such as cyanomethyl, carboxyalkyl such as carboxymethyl, alkoxycarbonylalkyl such as ethoxycarbonylmethyl, alkysulphonyloxyalkyl such as methylsulphonyloxyethyl, alkylaminoalkyl or dialkylaminoalkyl such as dimethylaminoethyl, alkoxylalkyl such as methoxymethyl alkylthioalkyl such as methylthiomethyl, haloalkyl or alkanoyl.

The heteroatom-containing substituent groups may also contain rings which are either carbocyclic or heterocyclic rings. A particular example of a group including a carbocyclic ring (for example phenyl or naphthyl) and a heteroatom is phenacyl. Alternatively, the carbocyclic ring may itself be substituted by heteroatom-containing groups, preferably 1-3, e.g. which contain 1-3 heteroatoms which are O, N or S. Particular examples are $C_1-C_4$ alkoxy (e.g. methoxy), OH, $NH_2$, COOH, SH, keto, formyl and methylsulphonyloxy. Heterocyclic substituent groups preferably contain 3 to 6 ring atoms, particularly, 3,5 or 6, and the ring heteroatoms, of which there are preferably 1-3, can be N, S or O. An example of such an R group is oxiranylmethyl. These rings may be substituted by at least one $C_1-C_4$ alkyl group, preferably methyl, or heteroatom-containing group and preferably by 1 or 2 of these groups. The substitution may be either at a ring carbon atom or heteroatom. These heteroatom-containing groups preferably contain 1-3 heteroatoms, which are O, N or S, and are for example, $C_1-C_4$ alkoxy (e.g methoxy), =O, OH, $NH_2$, COOH, SH and formyl. A particular example of an R group in this category is 5-uracilylmethyl, i.e. a thyminyl group.

The group X may but need not contain at least one heteroatom, preferably 1-3 heteroatoms, which may for example be N or O. Particular examples of such groups are $C_1-C_4$ alkoxy and $NO_2$. Other preferred groups X are halogeno e.g. fluoro or chloro, and methyl. The alkyl groups in aralkyl X substituents will usually have 1-4 carbon atoms. It is usually preferred that there be only one X substituent present on the ring and that it is located in the 2' position, the —CO—Y group being at the 1' position. Such preferred 2'-substituents are halogeno (F, Cl or Br), azido or trifluoromethyl. However, there may be more than one X substituent and when X is F, preferably the substitution can be 2',6'-difluoro.

Group Z is preferably —CH=CH— or —S—.

Particularly potent anti-cancer agents in accordance with the present invention are those where R represents propargyl, n=0 and Y represents a glutamic acid radical or a salt or ester thereof. In addition, the corresponding compounds where n = 1 and X is fluoro in the 2'-position show high activity.

As indicated above, the present invention covers the quinazoline derivatives in the form of their free acids and also in the form of pharmaceutically acceptable salts or esters of these acids, which can be partial salts and esters. Thus, in the case of the compounds containing glutamic acid and aspartic acid radicals, the mono ester mono acid and diester derivatives and corresponding salt forms are also covered. In addition, R groups containing COOH groups for example, can be in salt or ester form e.g. the ethyl ester. The salts of the present invention may be addition salts formed with physiologically acceptable inorganic or organic acids or bases, or quaternary ammonium salts but are preferably sodium salts, e.g. disodium salts. The esters are preferably lipophilic esters in which form the compound as a pro-drug may be transported to the site of a non-specific esterase before being degraded to the corresponding acid form. Examples of preferred esters are those with $C_1-C_{20}$ aliphatic groups, e.g. alkyl esters, preferably of 1 to 4 carbon atoms, especially the diethyl esters.

The compounds of the present invention may be prepared by a partial or complete deprotection process carried out on a compound of formula Ia wherein X, Z and n are as defined above, $R^2$ is equivalent to R R or is a group R in protected form $R^o$ is hydrogen or a protecting group, and Y' represents a group of formula a), b) c), d), or e) as defined above for Y or a salt of a said group or a said group in partially or completely protected form, the protecting group in Y' being a carboxyl protecting group e.g. an ester group or other protecting group, the compound of formula Ia containing at least one protecting group. If deprotection is carried out to remove more than one protecting group, the deprotections may be carried out simultaneously or in any order. Preferably $R^o$ is a group $R^1$ $CO.O.CH_2$— wherein $R^1$ is a straight or branched chain alkyl group or an aryl or aralkyl group, the preferred $R^1$ being tert.butyl.

Thus, for example, the acids and salts of the present invention can be prepared by complete deprotection of a compound of formula Ia, the partial esters can be prepared by deprotection of the lactam group and the $R^2$ group as necessary, with Y' either already being in partial ester form or being in completely esterified form which is then partially deprotected and the full esters can be prepared by deprotection of the lactam group and the $R^2$ group as necessary, with the Y' group in completely esterified form.

Deprotection of the group Y' in ester form to form an acid can, for example, be carried out by mild saponification using a base such as NaOH. The resultant acid may, if desired, subsequently be subjected to reaction with an acid or base to form a pharmaceutically acceptable salt. Most preferably the acid is allowed to react with NaOH to form the corresponding disodium salt. Alternatively, an acid product can be esterified, a salt product can be converted to an acid or ester or an ester product can be trans-esterified. It may be desirable to form a salt directly from an ester by the deprotection process; where the compound of formula Ia is in the form of a diester, the disodium salt of the compound of formula I may be formed by saponifying the diester with 3 moles NaOH aq per mole of diester and, when this reaction is complete, adding 1 mole HCl aq per mole of diester and preferably freeze-drying the product salt.

The particular protecting group containing $R^1$ will usually be chosen having regard to the nature of the R and Y' groups and the desired product, i.e. such that the conditions required to remove the $R^1$ group will not affect the unprotected R group and will not remove protecting ester groups in Y' where these are required in the final product. An example of an $R^1CO$ group is the pivaloyl group; the pivaloyloxymethyl group being removed in a saponification step using say NaOH to remove ester groups from Y'.

$R^2$ is, as indicated, either equivalent to R or is a desired group R in protected form. Thus, $R^2$ in the latter instance may for example contain the group COOH in ester form, or a group OH in $R^2$ can be protected by an acid group. Examples of such groups $R^2$ are ethoxycarbonylmethyl, 2-acetoxyethyl and 3-acetoxypropyl which are deprotected to carboxymethyl, 2-hydroxyethyl and 3-hydroxypropyl, respectively. These $R^2$ groups may, however, themselves be examples of R. Another example of a protected form of R is where the substituent $R^2$ does not merely contain an extra group, but where it is in a different form from the R group and undergoes conversion as the deprotection step. An example of this is given later where an $R^2$ group 2-hydroxy-3-bromopropyl undergoes a cyclisation reaction under the saponification conditions for removing ester groups from Y' and forms an oxiranylmethyl group R.

The protected compound of formula Ia can itself be prepared by a coupling reaction as follows:

wherein $R^0$, $R^2$, X, Z, n and $Y_1$ are as defined for the compound of formula Ia and X" is a leaving group, preferably halogeno (e.g. chloro or bromo), p-toluenesulphonate, methylsulphonate or trifluoromethylsulphonate. This conjugation is generally carried out in the presence of an acid acceptor e.g. calcium carbonate, potassium carbonate, 2,6-dimethylpyridine or triethylamine and in a solvent e.g. N,N-dimethylacetamide or cellosolve.

The amines of formula II above may be prepared by the direct reaction of a compound of formula $R^2X'$ (where $R^2$ is as defined above and X' is a leaving group, preferably halogeno (e.g. chloro or bromo), p-toluenesulphonate, methylsulphonate or trifluoromethylsulphonate) with N-(4-aminobenzoyl)-L-glutamate, -L-aspartate or -poly-L-glutamate in protected form.

An alternative method for forming the amine of formula II is that of Santi (see. J. Heterocyclic. Chem. 4, 475) using as starting material a 4-(((4-methylphenyl)-sulphonyl)amino)benzoate ester, e.g. the ethyl ester, which is allowed to react with a compound $R^2X'$ (where $R^2$ and X' are as defined above) to introduce the $R^2$ group onto the amino nitrogen. The ester is then saponified to the free acid, converted to the acid chloride and then coupled with a Y' group in protected, e.g. diester, form. The product is the amine of formula II bearing the protecting group $CH_3$—$C_6H_4$—SO on the amino group which can then be removed.

Where it is desired to prepare compounds of the invention containing substituents X, it is preferable to prepare first the corresponding N-(4-nitrobenzoyl)-L-glutamate, -L-aspartate or poly-L-glutamate in protected form containing the appropriate X substituent and to convert that by hydrogenation or reduction to the corresponding 4-amino derivative which is then allowed to react with $R^2X'$ to form an amine of formula II.

The reactants of formula III above wherein R=tert-.butyl.CO.O.$CH_2$ and X" is bromo may be prepared from the corresponding 6-methyl compound by the use of N-bromosuccinimide.

An alternative method for forming the protected compounds of formula Ia involves converting the $N^{10}$-unsubstituted conjugated compound in lactam protected form and Y' in protected form, with $R^2X'$ (where $R^2$ and X' are as defined above) in accordance with the following scheme:

The compound of formula Ib can itself be prepared by the following reaction:

wherein X" is as defined above. In this reaction, instead of the 6-$CH_2$-X" compound of formula III, it is possible to use the corresponding 6-formyl or 6-cyano compounds since the compound of formula IIa bears no R group on the amino group at this stage of the synthesis.

The present invention also provides a pharmaceutical composition which comprises a therapeutically effective amount of an anti-cancer agent as defined for the present invention and a pharmaceutically acceptable carrier or diluent. Experiments using mice having artificially implanted tumours have shown that intraperitoneal injection of anti-cancer agents of the present invention can produce an increase in mean survival time of the mice which is dose related. Further these animals did not lose a significant amount of weight or show other signs of toxicity while undergoing treatment with the drug.

The composition of the invention can, for example, be in a form suitable for parenteral (e.g. intravenous, intramuscular or intracavitary), oral, topical or rectal administration. Particular forms of the composition may be, for example, solutions, suspensions, emulsions, creams, tablets, capsules, liposomes or microreservoirs, especially compositions in sterile injectable form. The compound of the present invention can be used in a method of treating cancer in the human or animal body by administering it to a host. Therapeutically effective doses administered either once or repeatedly in man are considered to be in the range of 50–10000 mg/meter$^2$ body area for each dose preferably at least 500 mg/m$^2$, for instance up to 5000 mg/m$^2$ or more, repeated as necessary.

The compounds of the present invention show a wide range of antitumour activity against leukaemias, lymphoid malignancies and a spectrum of solid tumours, in particular carcinomas and sarcomas. Thus, in addition to their use as single agents, the compounds of the invention could be co-administered with, or contained in a mixed formulation with, for example, mitotic inhibitors (e.g. vincristine, vinblastine), alkylating agents (e.g. cyclophosphamide, melphalan, myleran, chlorambucil, mustine), anti-metabolites (e.g. 5-fluorouracil, 6-mercaptopurine, thioguanine, cytosine arabinoside, hydroxyurea), intercalating antibiotics (e.g. adriamycin, bleomycin), or enzymes (e.g. asparaginase).

The compounds of the present invention may also be used as a component of a combined modality treatment, for example including radiotherapy and/or surgery.

The invention will now be illustrated by the following, non-limiting Examples and with reference to the accompanying drawings in which.

EXAMPLE 1

Figure 1:
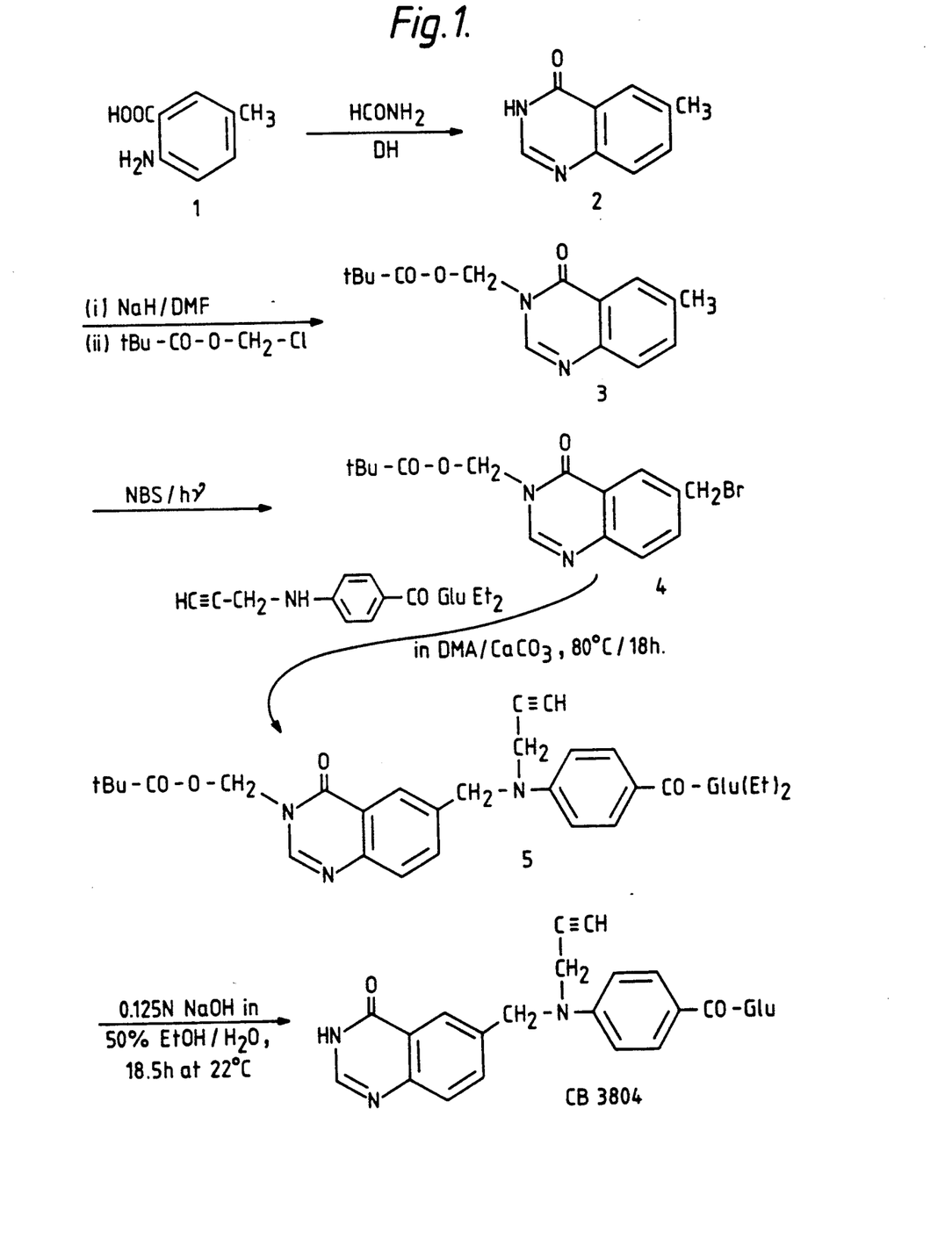
FIG. 1 outlines a synthesis of a compound of the invention (CB3804).

The 2-desamino analogue (CB3804) of N$^{10}$-propargyl-5,8-dideazafolic acid (CB 3717) was prepared by a synthesis as outlined in FIG. 1 of the accompanying drawings. The synthesis is described in detail below.

In these Examples, petrol refers to petroleum ether bp 60°–80° C.; TLC was performed using precoated sheets of silica gel 60F254 (Merck Art 5735); Melting points were determined on a Kofler block; NMR spectra were determined using Perkin Elmer R32 (90 MHz) and Bruker WM250 (250 MHz) spectrometers; Field strengths are expressed in units of δ(ppm) and peak multiplicities are designated thus: s, singlet; d, doublet; dd, doublet of doublets; t, triplet; bs, broad singlet; b, broad signal; m, multiplet. Absorption infra red spectra were taken on a Perkin Elmer 1310 spectrometer. Elemental analyses were determined by Butterworth Laboratories, Teddington, Middlesex. Results for the elements stated were within ±0.4%.

3,4-Dihydro-4-oxo-6-methylquinazoline (2) - 2-Amino-5-methylbenzoic acid (1) (Aldrich, 30.23g, 0.2 mole) and formamide (36.03g, 0.8 mole, 4 equiv.) were placed in a 400 mL beaker and stirred together to give a homogeneous, thick paste. The beaker was immersed in an oil bath such that the inner temperature came up to 130° C.; a dark-coloured liquid was obtained. The mixture was kept at 130° C. for 1 hour during which time ammonia gas was evolved followed by extensive solidification. The bath temperature was then raised to 180° C. and the mixture held thus for a further 1 hour, the large lumps of solid being broken up in an attempt to maintain thermal equilibrium and homogeneity. The mixture was cooled and treated with a mixture of ethanol (20 mL) and water (100 mL), and the lumps of solid broken up to give a homogeneous slurry. The product (28.8 g) was filtered off and washed twice and thoroughly with water. Recrystallisation from ethanol afforded white microneedles (24.76 g, 77.3%)

m.p. 260°–261° C. (Lit: Ehrlich, Ber. 34 3366 (1901) quotes 251° C.; Findeklee, Ber. 38 3553 (1905) quotes 255° C).

3,4-Dihydro-6-methyl-4-oxo-3-((pivaloyl)oxy)methylquinazoline (3)

Sodium hydride (60% dispersion in oil, 2.50 g, 0.0625 mole, 1.25 equiv.) was placed in a 500 mL 2-necked flask and rinsed with petrol. N,N-Dimethylformamide (Aldrich "Gold Label" grade dried over activated 3Å molecular sieves, 65 mL) was added followed by, with magnetic stirring, 3,4-dihydro-4-oxo-6-methylquinazoline (8.00 g, 0.05 mole) added over 15 minutes with occasional ice cooling. The neck of the flask was rinsed clean with further dimethylformamide (10 mL) and then sealed with a soda lime guard tube. Further stirring at room temperature for 30 minutes produced a clear, yellow-grey solution of the sodium salt containing a few specks of unreacted sodium hydride. To it chloromethyl pivalate (Aldrich, 97%, 7.80 g, 0.05 mole) was added during 2 minutes and the resulting mixture stirred at room temperature for 2 hours. The mixture, now containing precipitated sodium chloride, was partitioned between ether (1 L) and water (1 L). The ether extract was washed once with saturated brine (1 L), dried (MgSO$_4$) and concentrated in vacuo to give a yellow oil which crystallised spontaneously (13.80 g). This crude product was recrystallised from petrol (ca. 500 mL) filtering off some quinazoline starting material in the process. Crystallisation was allowed to complete overnight at 2° C. and the product then collected and washed once with petrol, (11.12 g, 81.1%), m.p. 108.5°–109° C., IR$\nu_{C=O}$ (ester) 1733 cm$^{-1}$ and $\nu_{C=O}$ (lactam) 1690 cm$^{-1}$.

NMR (90 MHz, CDCl$_3$/TMS)δ1.22 (s, 9H, tBu), 2.50 (s, 3H, methyl), 5.95 (s, 2H, methylene), 7.60 (distorted singlet, 2H, H$^7$ and H$^8$), 8.14 (distorted singlet, 1H, H$^5$), 8.22 (s, 1H, H$^2$). Anal. (C$_{15}$H$_{18}$N$_2$O$_3$) C,H,N.

6-Bromomethyl-3,4-dihydro-4-oxo-3-((pivaloyl)oxy)methylquinazoline (4)

The methyl compound (3) (6.86 g, 0.025 mole) was placed in a 1 L borosilicate flask and dissolved in carbon tetrachloride (250 mL) with the aid of brief warming. N-Bromosuccinimide (recrystallised from H$_2$O, 4.89 g, 0.0275 mole, 1.1 equiv.) was added and the mixture brought to reflux. The flask (entered only 1 cm into the heating mantle) was then irradiated from a distance of 5 cm with a 275 Watt sun-lamp for exactly 20 minutes. After cooling, the succinimide was filtered off and washed with carbon tetrachloride (2×50 ml). The combined filtrate and washings were concentrated to dryness to give a sticky, cream coloured solid (10.69 g). This was recrystallised from petrol (950 ml) during which process an insoluble solid (ca. 5%) was filtered off. Cooling to 2° C. gave unpretty white crystals (7.67 g, m.p. 104°-114° C.) which were recrystallised from petrol (1100 ml) to give more shapely crystals (6.74 g, 76.3%, m.p. 108°-115° C.) of technical grade product suitable for further use. A small portion of the technical product was recrystallised twice further from petrol to give the analytical sample, m.p. 121°-122° C., IR$\nu_{C=O}$ (ester) 1730 cm$^{-1}$ and $\nu_{C=O}$ (lactam) 1685 cm$^{-1}$, NMR (250 MHz, CDCl$_3$/TMS) δ1.20 (s, 9H, tBu), 4.60 (s, 2H, CH$_2$Br), 5.95 (s, 2H, CH$_2$), 7.70 (d, 1H, J$_{8,7}$=8.4 Hz, H$^8$), 7.82 (dd, 1H, J$_{7,8}$=8.4 Hz, J$_{7,5}$=2.2 Hz, H$^7$), 8.29 (s, 1H, H$^2$), 8.32 (d, 1H, J$_{5,7}$=2.2 Hz, H$^5$). Anal. (C$_{15}$H$_{17}$BrN$_2$O$_3$) C, H, N, Br.

Diethyl N-(4-(N-((3,4-dihydro-4-oxo-3-((pivaloyl)oxy)methyl-6-quinazolinyl)methyl)prop-2-ynylamino)benzoyl)-L-glutamate (5)

A mixture of the bromomethyl compound (4) 4 (technical quality, 2.30 g, at least 0.005 mole), diethyl N-(4-(prop-2-ynylamino)benzoyl)-L-glutamate, T. R. Jones, A. H. Calvert, A. L. Jackman, S. J. Brown, M. Jones, and K. R. Harrap: Europ. J. Cancer, 17 11 (1981), (1.80 g, 0.005 mole), calcium carbonate (dried at 100° C., 1.00 g, 0.01 mole) and N,N-dimethylacetamide (Aldrich "Gold Label" grade dried over activated 3Å molecular sieves, 20 mL) was stirred in a stoppered flask at 80° C. for 18 hours. After cooling the mixture was filtered through a bed of Celite and the solids washed thoroughly with dimethylacetamide. The clear filtrate was concentrated at 55° C./4 mm on a rotary evaporator and then at 75° C./1 mm by direct coupling to an oil pump to give a stiff brown gum (6.78 g). This was dissolved in a mixture of dichloromethane (13 mL) and ether (20 mL) and applied to a column of silica (Merck Art 15111, 240 g) made up in ether in a Jobin-Yvon Chromatospac Prep 10 machine. The solution was washed in with a mixture of CH$_2$Cl$_2$ (4 mL) and ether (6 mL) and the column then eluted with ether, the effluent passing through a Cecil 212A ultraviolet monitor set at 254 nm. The product eluted last of all and evaporation of the appropriate fractions yielded a gum (2.54 g, 80.3%) which, although pure, could not be induced to solidify. For characterisation a portion of the gum was dried at 100° C./P$_2$O$_5$/1 mm/18 hours to give a brittle glass.

NMR (250 MHz, CDCl$_3$/TMS)δ 1.20 (s, 9H, tBu), 1.22 (t, 3H, J =7.1 Hz, ethyl CH$_3$), 1.29 (t, 3H, J=7.1 Hz, ethyl CH$_3$), 3.02 (bs, 1H, ≡CH), 4.10 (q, 2H, J=7.1 Hz, ethyl CH$_2$), 4.16 (d, 2H, J=2.3 Hz, propargyl CH$_2$), 4.22 (q, 2H, J=7.1 Hz, ethyl CH$_2$), 4.74–4.83 (m, 1H, glu CHα), 4.76 (s, 2H, CH$_2$$^9$), 5.94 (s, 2H, O—CH$_2$—N), 6.85 (d, 3H, J=8.9 Hz, H$^{3'}$ & H$^{5'}$ with amidic NH superimposed), 7.71-7.75 (m, 4H, H$^7$, H$^8$, H$^{2'}$, H$^{6'}$), 8.25 (d, 1H, J$_{5,7}$=1.5 Hz, H$^5$), 8.26 (s, 1H, H$^2$).

Anal. (C$_{34}$H$_{40}$N$_4$O$_8$) C, H, N.

N-(4-(N-((3,4-dihydro-4-oxo-6-quinazolinyl)methyl)prop-2-ynylamino)benzoyl)-L-glutamic acid (CB 3804)

A mixture of the gummy triester (5)(0.633 g, 0.001 mole), H$_2$O (18 mL), EtOH (18 mL), and 1.00N NaOH$_{aq}$ (5 mL, 0.005 mole) was placed in a conical flask and stirred vigorously (magnetic stirrer) for 40 minutes to give a pale yellow solution. This solution was kept at 22° C. for 18.5 hours. It was then filtered through a bed of Celite (carbon treatment) and the clear filtrate acidified to pH 2.5 with 1.00 N HCl$_{aq}$. The resulting white gelatinous precipitate of the product was centrifuged (1500g/30 minutes) and washed by three cycles of resuspension (H$_2$0: 80 mL, 80 mL, and 40 mL)—centrifugation—decantation. The pellet was dried in vacuo over P$_2$O$_5$—first at 22° C./24 hours in a desiccator and then at 80° C./4 hours in a pistol. A pale yellow amorphous solid was obtained (0.312 g, 67.5%), m.p. 170°-173° C.

NMR (250 MHz, DMSO-D$_6$/TMS)δ3.22 (t, 1H, J=2.1 Hz, ≡CH$^{60}$), 3.4 (bs, 2H, water of hydration ), 4.36 (m, 3H, propargyl CH$_2$ & glu CHα), 4.81 (s, 2H, CH$_2$$^9$), 6.85 (d, 2H, J=8.9 Hz, H$^{3'}$ and H$^{5'}$), 7.65 (d, 1H, J$_{8,7}$=8.4 Hz, H$^8$ ), 7.75 (d, 2H, H$^{2'}$ & H$^{6'}$ superimposed upon dd, 1H, H$^7$ ), 8.03 (d, 1H, J$_{5,7}$=1.8 Hz, H$^5$ ), 8.06 (d, 1H, H$^2$), 8.27 (d, 1H, J=7.7 Hz, amidic NH ), 12.24 (bs, 3H, carboxyls & lactam NH ).

UV (taken in 0.1N NaOH$_{aq}$)λ(ε), maxima: 221 nm (34,500), 300 nm (29,000); minimum: 248 nm (6,200).

Anal. sample dried P$_2$O$_5$/110° C., (C$_{24}$H$_{22}$N$_4$O$_6$·1H$_2$0) C, H, N.

EXAMPLE 2

Figure 6:
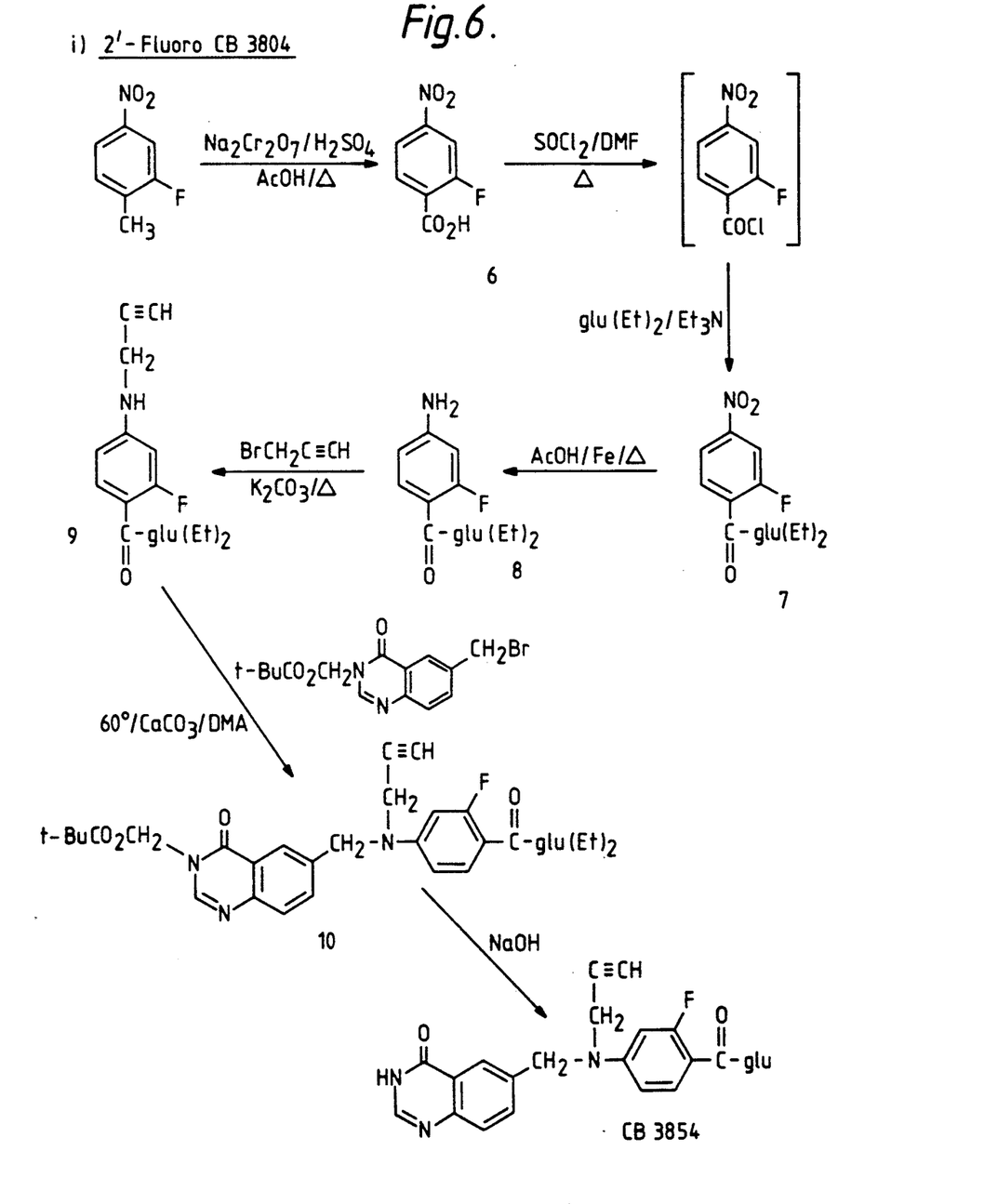
FIG. 6 outlines a synthesis of a compound of the invention (CB 3854).

The 2'-fluoro analogue (CB 3854) of CB 3804 was prepared by a synthesis as outlined in FIG. 6 of the accompanying drawings. The synthesis is described in detail below.

2-Fluoro-4-nitro-benzoic acid (6)

To a stirred glacial acetic acid solution of Na$_2$Cr$_2$O$_7$ (80.46 g, 0.26 mol) in a 2 l beaker was added 2-fluoro-4-nitrotoluene (31.03 g, 0.2 mol) followed during 10 minutes by concentrated H$_2$SO$_4$ (200 g). The initially bright orange solution became viscous and black and then boiled at just over 100° C. The resulting green slurry was heated for a further 1 hour at 90° C. Water (236 ml) was added and the resulting solution was cooled to 0° C. to give pale green crystals which were recovered by filtration and washed sparingly with cold water. The product (22.14 g) was recrystallised from water (200 ml) as pale green microneedles (21.16 g, 57.2%). M.P. 175°-178° C., Lit. F. C. Schmelkes and M. Rubin, J. Am. Chem. Soc. 66, 1631, (1944), 176°-177° C.

Diethyl-N-(2-fluoro-4-nitrobenzoyl)-L-glutamate (7)

A slurry of 2-fluoro-4-nitrobenzoic acid (6) (0.426 g, 2.3 mmol) in dry toluene (10 ml) was treated with SOCl$_2$ (0.41 g, 3.45 mmol) and the mixture heated under reflux for 1.5 hour with exclusion of moisture. After cooling and filtering through celite the pale buff coloured solution was concentrated on a rotary evaporator to give the acid chloride (quantitative yield) as a viscous brown oil which solidified on standing. A solution of the acid chloride in CH$_2$Cl$_2$ (50 ml) under a nitrogen atmosphere and maintaining a temperature below 25° C. was added during 15 minutes to a solution of diethyl L-glutamate hydrochloride (0.55 g, 2.3 mmol) and triethylamine 0.46g, 4.6 mmol) in CH$_2$Cl$_2$ (100 ml).

The resulting brown solution was stirred for a further 2 hours at 25° C., after which it was washed with H₂0 (2×250 ml), treated with decolourising charcoal and dried (MgSO₄) The extract was concentrated on a rotary evaporator to give a pale brown solid (0.76 g). This was recrystallised from toluene-cyclohexane (1:3, 20 ml) to give pure white needles (0.73 g, 85.9%), m.p. 80.5°-81.5° C. IR: 3370 and 3315 cm$^{-1}$ (N-H), and 1740 cm$^{-1}$ (C=0); MS: $m/z$ 168 and 122;

NMR (250 MHz CDCl₃/TMS), δ1.25 (t, J=7.1 Hz, 3H, CH₃), 1.33 (t, J=7.1 Hz, 3H, CH₃), 2.27 (m, 2H, glu CH₂), 2.47 (m, 2H, glu CH₂), 4.13 (q, J =7.1 Hz, 2H, ester CH₂), 4.27 (q, J =7.1 Hz, 2H, ester CH₂), 4.84 (m, 1H, glu CH), 7.50 (br t, J =7.6 and 7.6 Hz, 1H, amidic NH), 8.05 (dd, J =2.1 and 10.9 Hz, 1H, H³), 8.13 (dd, J =8.6 and 2.1 Hz, 1H, H⁵), 8.26 (dd, J = 8.6 and 7.4 Hz, 1H, H⁶), Anal. (C₁₆H₁₉FN₂O₇) C,H,F,N.

Diethyl N-(2-fluoro-4-aminobenzoyl)-L-glutamate (8)

A solution of the nitro compound (7) (9.26 g, 25 mmol) in AcOH (50 ml) was treated with iron powder (Aldrich 325 mesh, 6.14 g, 0.11 g atom). The slurry was kept mobile with overhead stirring at 50° C. for 2 hours. The mixture was cooled to room temperature and treated with CH₂Cl₂ (250 ml) and H₂0 (1000 ml) and the mixture then filtered. The organic layer was separated and washed with H₂0 (1000 ml); treated with decolourising charcoal, dried (MgSO₄) and concentrated to give a dirty white crystalline solid (11.3 g). Recrystallisation from toluene-hexane (5:1.5, 65 ml) gave fluffy off-white crystals (8.12 g, 95.5%), m.p. 129.5°-131.5° C.

IR: 1730 cm$^{-1}$ (C=0); MS: $m/z$ 340 (M+);

NMR (250 MHz, CDCl₃/TMS),δ1.23 (t, J=7.1 Hz, 3H, CH₃), 1.30 (t, J=7.1 Hz, 3H, CH₃), 2.22 (m, 2H, glu CH₂), 2.44 (m, 2H, glu CH₂), 4.11 (q, J=7.1 Hz, 2H, ester CH₂) 4.23 (q, J=7.1 Hz, 2H, ester CH₂) 4.25 (br s, 2H, NH₂), 4.83 (m, 1H, glu CH), 6.33 (dd, J=14.3 and 2.2 Hz, 1H, H³), 6.47 (dd, J=8.6 and 2.2 Hz, 1H, H⁵), 7.19 (dd, J=13.8 and 7.5 Hz, 1H, amidic NH), 7.81 (t, J=8.6 and 8.6 Hz, 1H, H⁶), Anal. (C₁₆H₂₁FN₂O₅) C,H,F,N.

Diethyl N-(2-fluoro-4-(N-prop-2-ynylamino)benzoyl)-L-glutamate (9)

To a DMF solution of the amino compound (8) (7.49 g, 22 mmol) was added K₂CO₃ (3.04 g, 22 mmol) and propargyl bromide (80% w/v solution in toluene, 6.54 g, 44 mmol). The mixture was heated to 110°-120° C. for 3 hours with vigorous stirring in the absence of moisture. After cooling, the solvent was removed to give a dark brown viscous slurry. This was added to EtOAc (250 ml) and washed with H₂0 (250 ml). The brick red organic layer was subsequently dried (MgSO₄) and concentrated to give a dark red syrup (10.0 g). A solution in petrol-EtOAc-CH₂Cl₂ (2:1:1, 25 ml) was applied to a glass column (5 cm i.d.) of silica gel (Merck Art 9385, 450 g). After elution with petrol-EtOAc (2:1, 2 1) followed by petrol-EtOAc (1.5:1), concentration of the appropriate fractions yielded a pale yellow oil (5.03 g, 60.5%)

IR: 3310 cm$^{-1}$ (NH) and 1745 cm$^{-1}$ (C=0); MS: $m/z$ 378 (M+);

NMR (250 MHz, CDCl₃/TMS).δ1.23 (t, J=7.1 Hz, 3H, CH₃), 1.30 (t, J=7.1 Hz, 3H, CH₃), 2.22 (m, 2H, glu CH₂), 2.27 (t, J=2.4 Hz, 1H, acetylenic), 2.44 (m, 2H, glu CH₂), 3.97 (s, 2H, propargyl CH₂), 4.11 (q, J=7.1 Hz, 2H, ester CH₂) 4.22 (q, J=7.1 Hz, 2H, ester CH₂) 4.54 (br s, 1H, amine NH), 4.84 (m, 1H, CH), 6.36 (dd, J=14.7 and 2.2 Hz, 1H, H³), 6.50 (dd, J=8.7 and 2.3 Hz, 1H, H⁵), 7.21 (dd, J=7.6 and 6.2 Hz, 1H, amidic NH), 7.91 (t, J=8.9 and 8.9 Hz, 1H, H6), Anal. (C₁₉H₂₃FN₂O₅) C,H,F,N.

Diethyl N-(2-fluoro-4-(N-((3,4-dihydro-4-oxo-3((pivaloyl)oxy)-methyl-6-quinazolinyl)methyl)prop-2-ynylamino)benzoyl)-L-glutamate (10)

The compound was prepared from compound (9) in a similar manner to that for the preparation of compound (5) from compound (4) in Example 1 using the reagent quantities and conditions set out in Table A.

An analytical sample was dried at 70° C./P₂O₅/0.1 mm/7 hours. MS: M/Z 650 (M+);

NMR (250 MHz, DMSO-D₆/TMS),δ1.11 (s, 9H, tBu), 1.15 (t, J=7.1 Hz, 3H, CH₃), 1.18 (t, J=7.1 Hz, 3H, CH₃), 2.01 (m, 2H, glu CH₂), 2.39 (m, 2H, glu CH₂), 3.27 (t, J=1.7 Hz, 1H, acetylenic), 4.03 (q, J=7.1 Hz, 2H, ester CH₂) 4.10 (q, J=7.1 Hz, 2H, ester CH₂) 4.39 (m, 2H, propargyl CH₂), 4.39 (m, 1H, glu CH₂), 4.84 (s, 2H, CH⁹₂), 5.89 (s, 2H, O—CH₂-N), 6.63 (dd, J=12.6 and 2.1 Hz, 1H, H³'), 6.67 (dd, J=8.9 and 2.1 Hz, 1H, H⁵ ), 10 7.50 (t, J=8.9 and 8.9 Hz, 1H, H⁶'), 7.68 (d, J=8.3 Hz, 1H, H⁸), 7.78 (dd, J=8.3 and 1.8 Hz, 1H, H⁷), 8.09 (d, J =1.8 Hz, 1H, H⁵), 8.13 (dd, J=7.2 and 3.9 Hz, 1H, amidic NH).

Anal. (C₃₄H₃₉FN₄O₈) C,H,F,N.

N-(2-Fluoro-4-(N-((3,4-dihydro-4-oxo-6-quinazolinyl)-methyl)prop-2-ynylamino)benzoyl)-L-glutamic acid (CB 3854)

This compound was prepared from compound (10) in a similar manner to that for the preparation of CB 3804 from compound 5 in Example 1 using the reagent quantities and conditions set out in Table B.

M.P. 185°-188.5° C;

NMR (250 MHz, DMSO-D₆/TMS),δ1.98 (m, 2H, glu CH₂), 2.31 (m, 2H, glu CH₂), 3.26 (t, 2.0 Hz, 1H, acetylenic), 4.37 (m, 2H, propargyl CH₂), 4.37 (m. 1H, glu CH), 4.82 (s, 2H, CH⁹₂) 6.63 (dd, J=14.3 and 2.2 Hz, 1H, H³'), 6.68 (dd, J=8.9 and 2.2 Hz, 1H, H⁵'), 7.54 (t, J=8.9 and 8.9 Hz, 1H, H⁶'), 7.64 (d, J=8.3 Hz, 1H, H⁸), 7.73 (dd, J=8.3 and 2.0 Hz, 1H, H⁷), 7.97 (t, J=6.3 Hz, 1H, amidic NH), 8.02 (d, J=2.0 Hz, 1H, H⁵), 8.07 (s, 1H, H²), 12.25 (br s, 1H, lactam NH), 12.47 (br s, 2H, COOH's), UV (0.1N NaOH$_{aq}$)λ(ε), maxima: 222.5nm (31,700), 298nm (30,300); minimum: 247.5nm (6,800).

Anal. (C₂₄H₂₁FN₄O₆.1H₂0) C,H,F,N.

EXAMPLE 3

Figure 7:
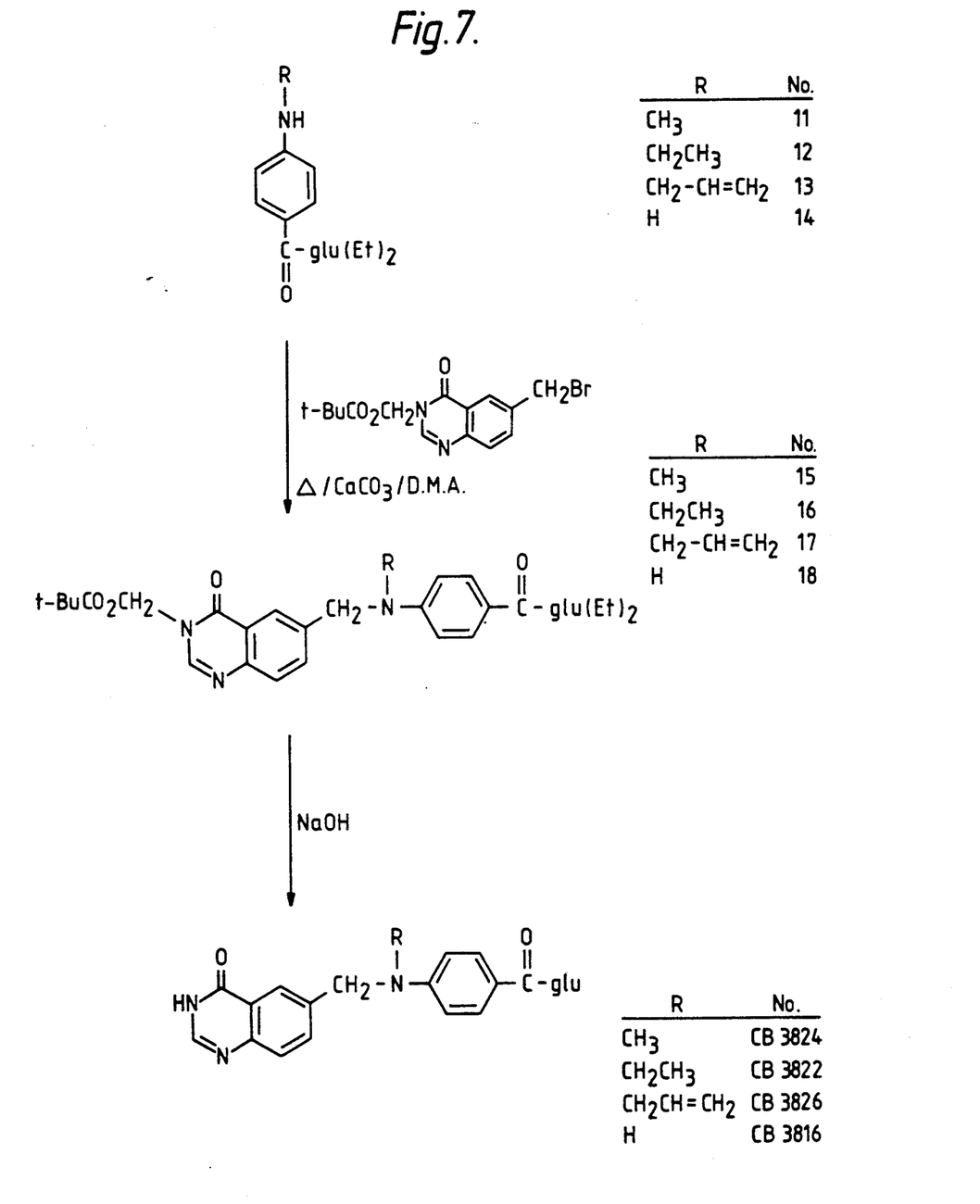
FIG. 7 outlines the synthesis of four compounds of the invention (CB3824, 3822, 3826, 3816).

The derivative of 2-desamino-5,8-dideazafolic acid with a —CH₃ substituent at N¹⁰ (CB 3824) is shown in FIG. 7. It was prepared in a similar manner to CB 3804. The synthesis is described below:

Diethyl N-(4-(methylamino)benzoyl)-L-glutamate (11)

To a DMF solution of diethyl N-(4-aminobenzoyl)-glutamate (9.66 g, 30 mmol) was added K₂CO₃ (4.14 g, 30 mmol) and iodomethane (6.81 g, 48 mmol). The mixture was stirred vigorously in the absence of moisture for 26 hours. After removal of solvent under oil pump vacuum, the pale brown sludge was added to EtOAc (250 ml) and washed with H₂0 (2×250 ml). The organic layer was subsequently dried over MgSO₄ and evaporated in vacuo to give a pale brown oil (10.7 g). This was dissolved in 5% EtOAc in CH$_2$Cl$_2$ (20 ml) and applied to a column of silica gel (Merck Art. 7734, 450 g) made up in a glass column (i.d. 5 cm). The column was eluted with cyclohexane: CH$_2$Cl$_2$ EtOAc (4:4:2.5) and the appropriate fractions were evaporated in vacuo to give a pale yellow oil (2.32 g, 23%). This solidified on standing to give an off-white crystalline solid. Recrystallisation from toluene:hexane (10:1.5, 10 ml) gave fine pure white crystals (2.2 g). M.P. 89.5°–91.5° C.; a crude preparation of (11) has been described by D.V. Santi, (1967): J. Heterocyclic Chem. 4, 475.

Diethyl N-(4-(N-((3,4-dihydro-4-oxo-3-((pivaloyl)oxy) methyl-6-quinazolinyl)methyl)methylamino)benzoyl)-L-glutamate (15)

This compound was prepared from compound (11) in a manner similar to that described for the preparation of compound (5) using the reagent quantities and conditions set out in Table A.

For characterisation a portion was dried at 70° C. /P$_2$O$_5$/1 mm/8 hour to give a brittle glass. M.P. 86.5°–90° C.

NMR (250 MHZ, DMSO-D$_6$/TMS).δ1.11 (s, 9H, tBu), 1.16 (t, J=7.1 Hz, 3H, CH$_3$), 1.18 (t, J=7.1 Hz, 3H, CH$_3$), 2.05 (m, 2H, glu CH$_2$), 2.41 (m, 2H, glu CH$_2$), 3.14 (s, 3H, N$^{10}$CH$_3$), 4.04 (q, J=7.1 Hz, 2H, ester CH$_2$), 4.09 (q, J=7.1 Hz, 2H, ester CH$_2$), 4.38 (m, 1H, glu CH), 4.83 (s, 2H, CH$^9{}_2$) 5.89 (s, 2H, O—CH$_2$—N), 6.77 (d, J=9.0 Hz, 2H, H$^{3'}$, H$^{5'}$), 7.68 (m, 2H, H$^7$, H$^8$), 7.22 (d, J=9.0 Hz, 2H, H$^{2'}$, H$^{6'}$), 7.98 (s, 1H, H$^5$), 8.33 (d, J=6.8 Hz, 1H, amidic NH), 8.43 (s, 1H, H$^2$).

Anal. (C$_{32}$H$_{40}$N$_4$O$_8$) C,H,N.

N-(4-(N-((3,4-dihydro-4-oxo-6-quinazolinyl)methyl) methylamino)benzoyl)-L-glutamic acid (CB 3824)

This compound was prepared from compound (15) in a manner similar to that for the preparation of CB 3804 in Example 1 using the reagent quantities and conditions set out in Table B.

M.P 186.5°–189° C.

NMR (250 MHz, DMSO-D$_6$/TMS)δ1.99 (m, 2H, glu CH$_2$), 2.33 (m, 2H, glu CH$_2$), 3.13 (s, 3H, N$^{10}$CH$_3$), 4.35 (m, 1H, glu CH), 4.81 (s, 2H, CH$^9{}_2$), 6.77 (d, J=8.9 Hz, 2H, H$^{3'}$, H$^{5'}$), 7.65 (s, 2H, H$^7$, H$^8$), 7.73 (d, J=8.9 Hz, 2H, H$^{2'}$, H$^{6'}$), 7.91 (s, 1H, H$^5$), 8.06 (s, 1H, H$^2$), 8.21 (d, J=7.7 Hz, 1H, amidic NH), 12.25 (br s, 1H, lactam NH), 12.35 (br s, 2H, COOH's)

UV (0.1N NaOH$_{aq}$) λ(ε); maxima: 222.5 nm (31,600), 310nm (30,200); minimum: 248nm (5,200).

Anal. (C$_{22}$H$_{22}$N$_4$O$_6$.1H$_2$O) C,H,N.

EXAMPLES 4, 5 AND 6

In a similar manner to the preparation of CB 3804, the compounds CB3822, 3826 and 3816 were also prepared by alkylation of the appropriate amine; followed by saponification according to the scheme in FIG. 7 and using reagent quantities and conditions as shown in Tables A and B.

Diethyl N-(4-(ethylamino)benzoyl-L-glutamate (12)

To a DMF solution of diethyl N-(4-aminobenzoyl)-glutamate (6.44 g, 20 mmol) was added K$_2$CO$_3$ (2.76 g, 20 mmol) and iodoethane (6.24 g, 40 mmol). The mixture was stirred vigorously at 100°–110° C. for 5 hours. After removal of the solvent under oil pump vacuum, the dark brown sludge was added to EtOAc (250 ml) and washed with H$_2$O (2×500 ml). The organic layer was subsequently dried (MgSO$_4$) and evaporated under vacuum to give a brown oil (8.4 g). This was dissolved in 5% EtOAc in CH$_2$Cl$_2$ (10 ml) and applied to a column of silica gel (Merck Art. 7734, 400 g) made up in a glass column (i.d. 5 cm). The column was eluted with 5% EtOAc in CH$_2$Cl$_2$ and the appropriate fractions were concentrated to give a golden coloured oil (4.56 g, 65.1%) which solidified to give a pale yellow solid. M.P. 77°–78° C., Lit. 73° C., J. A. Montgomery, J. R. Piper, R. D. Elliott, C. Temple Jr., E. C. Roberts, and Y. F. Shealy, (1979); J. Med. Chem. 22, 862.

Diethyl N-(4-(N-((3,4-dihydro-4-oxo-3-((pivaloyl)oxy) methyl-6-quinazolinyl)methyl)ethylamino)benzoyl)-L-glutamate (16)

For characterisation a portion was dried at 70° /P$_2$O$_5$/1 mm/8 hours to give a brittle glass.

MS: m/z 622 M+;

NMR (250 MHz, CDCl$_3$/TMS)δ1.11 (s, 9H, tBu), 1.15 (t, J=6.9 Hz, 3H, ethyl CH$_3$), 1.17 (t, J=7.0 Hz, 6H, CH$_3$'s) 2.04 (m, 2H, glu CH$_2$), 2.40 (m, 2H,glu CH$_2$), 3.59 (q, J=6.9, 2H, ethyl CH$_2$), 4.03 (q, J=7.0, 2H, ester CH$_2$), 4.08 (q, J=7.0, 2H, ester CH$_2$), 4.38 (m, 1H, glu CH), 4.78 (s, 2H, CH$^9{}_2$), 5.89 (s, 2H, O—CH$_2$—N), 6.71 (d, J=8.9 Hz, 2H, H$^{3'}$, H$^{5'}$), 7.69 (d, J=8.9 Hz, 2H, H$^{2'}$, H$^{6'}$), 7.69 (m, 2H, H$^7$, H$^8$), 8.00 (s, 1H, H$^5$), 8.29 (d, J=7.5 Hz, 1H, amidic NH), 8.43 (s, 1H, H$^2$).

Anal. (C$_{33}$H$_{42}$N$_4$O$_8$) C,H,N.

N-(4-(N-((3,4-dihydro-4-oxo-6-quinazolinyl)methyl) ethylamino)benzoyl)-L-glutamic acid (CB 3822)

M.P. 143.5°–145.5° C., NMR (250 MHz, DMSO-D$_6$/TMS) 1.17 (t, J=6.9 Hz, 3H, CH$_3$), 1.98 (m, 2H, glu CH$_2$), 2.32 (m, 2H, glu CH$_2$), 3.58 (q, J=6.9 Hz, 2H, ethyl CH$_2$), 4.34 (m, 1H, glu CH), 4.75 (s, 2H, CH$^9{}_2$), 6.71 (d, J=8.9 Hz, 2H, H$^{3'}$, H$^{5'}$), 7.66 (m, 2H, H$^7$, H$^8$), 7.70 (d, J=8.9 Hz, 2H, H$^{2'}$,H$^{6'}$), 7.93 (s, 1H, H$^5$), 8.06 (s, 1H, H$^2$), 8.17 (d, J=7.7 Hz, 1H, amidic NH), 12.24 (s, 1H, lactam NH), 12.29 (br s, 2H, COOH's)

UV (0.1N NaOH$_{aq}$) λ(ε), maxima: 224nm (30,800), 312nm (29,900); minimum 250nm (5,500).

Anal. (C$_{23}$H$_{24}$N$_4$O$_6$.1H$_2$O) C,H,N.

Diethyl N-(4-(N-((3,4-dihydro-4-oxo-3-((pivaloyl)oxy) methyl-6-quinazolinyl)methyl)prop-2-enylamino)benzoyl)-L-glutamate (17)

This was synthesised by reaction of the compound (4) and diethyl N-(4-(prop-2-enylamino)benzoyl)-L-glutamate Lit. T. R. Jones, A. H. Jackman, S. J. Brown, M. Jones and K. R. Harrap: Europ. J. Cancer, 17 11 (1981). For characterisation a portion was dried at 70° C./P$_2$O$_5$/1 mm/10 hours to give a brittle glass.

M.P. 47°–50° C. MS: m/z 634 (M+),

NMR (250 MHz, DMSO-D$_6$/TMS),δ1.11 (s, 9H, tBu), 1.15 (t, J=7.1 Hz, 3H, ester CH$_3$), 1.17 (t, J=7.1 Hz, 3H, ester CH$_3$), 2.03 (m, 2H, glu CH$_2$), 2.40 (m, 2H, glu CH$_2$), 4.03 (q, J=7.1 Hz, 2H, ester CH$_2$), 4.07 (q, J=7.1 Hz, 2H, ester CH$_2$), 4.19 (m, 2H, allyl CH$_2$), 4.37 (m, 1H, glu CH), 4.79 (s, 2H, CH$^9{}_2$), 5.18 (m, 2H, terminal allyl CH$_2$), 5.85–5.96 (m, 1H, allyl CH), 5.89 (s, 2H, O—CH$_2$—N), 6.72 (d, J=8.9 Hz, 2H, H$^{3'}$, H$^{5'}$) 7.68 (d, J=8 9 Hz, 2H, H$^{2'}$, H$^{6'}$), 7.73 (m, 2H, H$^7$, H$^8$), 8.01 (d, J=1.5 Hz, 1H, H$^5$), 8.31 (d, J=7.4 Hz, 1H, amidic NH), 8.44 (s, 1H, H$^2$).

Anal. (C$_{34}$H$_{42}$N$_4$O$_8$.1H$_2$O) C,H,N.

N-(4-(N-((3,4-dihydro-4-oxo-6-quinazolinyl)methyl)-prop-2-enylamino)benzoyl)-L-glutamic acid (CB 3826)

M.P. 138°-143° C.

NMR (250 MHz, DMSO-D$_6$),$\delta$1.98 (m, 2H, glu CH$_2$), 2.09 (m, 2H, glu CH$_2$), 4.18 (m, 2H, allyl CH$_2$), 4.34 (m, 1H, glu CH), 4.77 (s, 2H, CH$^9_2$), 5.18 (m, 2H, terminal allyl CH$_2$), 5.83-5.96 (m, 1H, allyl CH), 6.72 (d, J=8.9 Hz, 2H, H$^{3'}$, H$^{5'}$), 7.67 (m, 2H, H$^7$, H$^8$), 7.68 (d, J=8.9 Hz, 2H, H$^{2'}$, H$^{6'}$), 7.94 (s, 1H, H$^5$), 8.06 (s, 1H, H$^2$), 8.19 (d, J=7.7 Hz, 1H, amidic NH), 12.25 (s, 1H, lactam NH), 12.31 (br s, 2H, COOH's), UV (0.1N NaOH$_{aq}$) $\lambda(\epsilon)$, maxima: 220.5nm (33,700), 310nm (30,700); minimum 250nm (5,700).

Anal. (C$_{24}$H$_{24}$N$_4$O$_6$ 3/4H$_2$O) C, H, N

Diethyl N-(4-(((3,4-dihydro-4-oxo-3-((pivaloyl)oxy)methyl-6-quinazolinyl)methyl)amino)benzoyl)-L-glutamate (18)

This was synthesised by alkylation of (4) and diethyl N-(4-(aminobenzoyne)-L-glutamate (14).

M.P. 63°-66° C.

NMR (250 MHz, CDCl$_3$/TMS),$\delta$1.20 (s, 9H, tBu), 1.21 (t, 3H, CH$_3$), 1.29 (t, 3H, CH$_3$), 2.21 (m, 2H, glu CH$_2$), 2.46 (m, 2H, glu CH$_2$), 4.09 (q, 2H, ester CH$_2$), 4.21 (q, 2H, ester CH$_2$), 54 (s, 2H, CH$^9_2$), 4.64 (br s, 1H, N$^{10}$H), 4.77 (m, 1H, glu CH), 5.94 (s, 2H, 0—CH$_2$—N), 6.61 (d, J=8.7 Hz, 2H, H$^{3'}$, H$^{5'}$), 6.78 (d, J=7.6 Hz, 1H, amidic NH), 7.66 (d, J=8.7 Hz, 2H, H$^{2'}$, H$^{6'}$), 7.71 (d, J=8.4 Hz, 1H, H$^8$), 7.78 (dd, J=8.4 and 1.9 Hz, 1H, H$^7$), 8.27 (s, 1H, H$^2$), 8.30 (d, J=1.9 Hz, 1H, H$^5$), Anal. (C$_{31}$H$_{38}$N$_4$O$_8$) C,H,N.

N-(4-(((3,4-dihydro-4-oxo-6-quinazolinyl)methyl)amino) benzoyl)-L-glutamic acid (CB 3816)

NMR (250 MHz, CD$_3$OD/TMS),$\delta$2.17 (m, 2H, glu CH$_2$), 2.44 (t, 2H, glu CH$_2$), 4.54 (s, 2H, CH$^9_2$), 4.80 (s, 2H, glu CH), 4.90 (br s, 1H, N$^{10}$H), 6.63 (d, J=8.8 Hz, 2H, H$^{3'}$, H$^{5'}$), 7.64 J=8.8 Hz, 2H, H$^{2'}$, H$^{6'}$), 7.67 (d, J=8.4 Hz, 1H, H$^8$), 7.85 (dd, J=8.4 and 2.0 Hz, 1H, H$^7$), 8.06 (s, 1H, H$^2$), 8.22 (d, J=2.0 Hz, 1H, H$^5$), Lactam NH and COOH's not recorded.

UV (taken in 0.1N NaOH$_{aq}$)$\lambda(\epsilon)$, maxima: 288 nm (24,100), 220 nm (30,100); minima: 247 nm (7,250).

Anal. (C$_{21}$H$_{20}$N$_4$O$_6$) C,H,N

EXAMPLE 6

N-(5-(N-((3,4-dihydro-4-oxo-6-quinazolinyl)methyl)-prop-2-ynylamino)thien-2-oyl)-L-glutamic acid CB3866 a) Diethyl N-(5-(prop-2-ynylamino)thien-2-oyl)-L-glutamate

N-(5-amino-thien-2-oyl)-L-glutamate (5g) was dissolved in dry dimethyformanide (100ml), propargyl bromide (2.5g of 80% solution toluene) and 2,6-lutidine (2.0ml) added and the mixture stirred at 40 C. for 48 hrs. After cooling to room temperature the mixture was poured into water (500 ml), extracted with ethyl acetate (3×100 ml) and the combined organic extract washed with water 2×50ml), dried over magnesium sulphate and evaporated in vacuo. The resulting oil was chromotographed on silica gel (250g) using 15% ethyl acetate/methylene chloride as eluent to give diethyl N-(5(prop-2-ynylamino)thien-2-oyl)-L-glutamate.

The N-(5-aminothien-2-oyl)-L-glutamate was itself prepared as follows:

5-nitrothien-2-oyl chloride (3g) was dissolved in toluene (50ml), (L)-glumatic acid diethyl ester (hydrochloride salt) (4.15g) was added followed by pyridine (1.5g). The mixture was stirred at room temperature for 72 hours, poured into water (200ml), extracted with ethyl acetate (3×100ml) and the combined extracts washed with brine (50ml) dried over magnesium sulphate and evaporated in vacuo. Resulting oil was purified by chromatography on silica gel using 10% ethyl acetate/methylene chloride as eluent and the product thus obtained dissolved in ethanol (20ml) and added slowly to a sodium hydrosulphite (6.2g of dihydrate salt) solution in water maintained at 0° C. After stirring for one hour, the mixture was diluted with water (100ml), extracted with ethyl acetate (3×50ml) and the combined extracts washed with brine (2×50ml) dried over magnesium sulphate and evaporated in vacuo. The resulting oil was purified by chromatography on silica gel (100g) using 27% ethyl acetate/methylene chloride as eluent to give N-(5-aminothien-2-oyl)-(L)-glutamate which was used in subsequent reactions without further purification.

b) The product of step (a) was reacted with bromomethyl compound (4) as described in Example 1 and the resulting diethyl N-(5-(N-((3,4-dihydro-4-oxo-3-((pivaloyl)oxy)methyl-6-quinazolinyl)methyl)prop-2-

TABLE A

| | Preparation of antifolate triesters. | | | | | | | |
|---|---|---|---|---|---|---|---|---|
| Compd. | amine mmol | quinazoline 4 mmol | CaCO$_3$ mmol | D.M.A. ml | reaction temp °C. | reaction time/h | chromatography | yield % |
| 10 | 5.30 | 5.00 | 10.60 | 17 | 60 | 18 | CH$_2$Cl$_2$:EtOAc; 10.1 | 89.9 |
| 15 | 6.54 | 5.95 | 11.90 | 20 | 50 | 24 | CH$_2$Cl$_2$:cyclohexane EtOAc; 3:3:2 | 89.3 |
| 16 | 2.50 | 2.75 | 5.00 | 10 | 50 | 29 | Et$_2$O | 92.2 |
| 17 | 1.21 | 1.21 | 2.42 | 5 | 50 | 48 | CH$_2$Cl$_2$:EtOAc; 4:1 | 56.3 |
| 18 | 1.00 | 1.00 | 2.00 | 3.3 | 60-70 | 24 | 40-50% EtOAc in CH$_2$Cl$_2$ | 57.7 |

((pivaloyl)oxy)methyl-6-quinazolinyl)methyl)prop-2-

TABLE B

| | Preparation of antifolate diacids | | | | | |
|---|---|---|---|---|---|---|
| Compound | starting matl/mmol | NaOH (aq) mol eq. | reaction time, h | acidified to pH | washing cycles | drying temp °C. | yield % |
| CB3824 | 4.35 | 4.8 | 24 | 3.5 | 2 | 70 | 62.1 |
| CB3822 | 1.35 | 5 | 18 | 3.4 | 3 | 70 | 58.5 |
| CB3826 | 0.435 | 5 | 24 | 3.22 | 2 | 70 | 77.0 |
| CB3816 | 0.42 | 5 | 20 | 3.5 | 2 | — | 63.6 |
| CB3854 | 3.00 | 5 | 24 | 3.24 | 3 | 70 | 14.6 | ynylamino)thien-2-oyl-L-glutamate hydrolysed, as described in Example 1 for the corresponding benzoyl analogue, to give CB 3866.

THE COMPARATIVE PHARMACOKINETICS AND TOXICITY OF CB3804 AND CB3717

Studies have been performed in mice and rats.

Mice

CB3717 and CB3804 were dissolved in 0.15M NaHCO$_3$ pH 9-9.5 at either 10, 30 or 50 mg/ml. The compounds were administered i.p. to male BDFl mice at 10 ml/kg to give doses of 100, 300 or 500 mg/kg. 3 Hours and 6 hours after administration groups of three mice at each dose level were sacrificed by exsanguination via cardiac puncture. Plasma was prepared and the livers and kidneys excised and weighed. Concentrations of CB3717 and CB3804 were determined in the plasma, livers and kidneys by high performance liquid chromatography.

As shown in Table 1, CB3717 was readily detected in the plasma, liver and kidneys of all of the mice sacrificed. In contrast, at the time points studied, CB3804 levels were below the limit of detection with the exception of plasma levels 3 hours after administration of CB 3804 at 500 mg/kg.

Samples of plasma were also analysed for the enzyme alanine transaminase, an indicator of hepatotoxicity. As shown in Table 2, levels of alanine transaminase were markedly elevated following CB3717 treatment, however, following CB3804 administration the levels were within the normal range (5-25U/l).

To demonstrate that CB3804 is absorbed following i.p. administration an excretion experiment was performed in which mice received 100 mg/kg CB3804 i.p. As shown in Table 3, there was elimination of CB3804 in both the faeces and urine. In addition, two components were observed in faeces which may represent CB3804 metabolites. Comparative data for CB3717 are also given in Table 3. These excretion studies indicate that there is satisfactory bioavailability of CB3804 following i.p. administration and hence the lack of hepatotoxicity and the failure to detect CB3804 in the kidneys are properties inherent in the compound.

Rats

CB3717 and CB3804 were dissolved in 0.15M NaHCO$_3$ pH9 and administered at 100 mg/kg as 1 hour i.v. infusion to pentobarbital anaesthetised female Wistar rats. During and after the infusion blood and bile samples were collected. Four hours after the experiment the rats were sacrificed and the urine collected from the bladder and the liver and kidneys removed.

The samples were analysed for CB3717 and CB3804 by HPLC. As shown in Table 4, CB3717 was cleared less rapidly from the plasma of rats than CB3804. This accords with the greater biliary and urinary excretion of CB3804. In contrast to CB3717, no CB3804 could be detected in either the liver or kidneys at the end of the experiment. Samples of plasma were also analysed for alanine transaminase. As shown in Table 4, CB3717 produced pronounced elevation in plasma levels of this enzyme whereas CB3804 did not.

Conclusion

On the basis of these experiments we conclude that at the doses studied CB3804 is not hepatotoxic in mice or rats. This is in marked contrast to CB3717.

Similarly, CB3804 does not apparently accumulate in the kidneys. As CB3717 renal toxicity is thought to be due to precipitation of the drug in the kidney, CB3804 should represent a non-nephrotoxic quinazoline.

ACTIVITY IN VITRO AND IN VIVO OF COMPOUNDS OF THE INVENTION AND CB 3717.

Enzymology

Each compound was dissolved in 0.15M NaHCO$_3$. Thymidylate synthetase was assayed by a $^3$H release method. A 50,000 g supernatant was prepared from a TS over-producing (45-fold) L1210 cell line that was developed in this Institute. The preparation buffer was 0.05M potassium phosphate/0.01M 2-mercaptoethanol, pH 7.4. The 0.5 ml incubation mixture contained 0.05 ml inhibitor, 0.20 ml supernatant (about 10ug supernatant protein), 50 uM $^3$H dUMP, (0.22 uCi) and 200 uM ($\pm$)-L-5,10-CH$_2$FH$_4$ (made by dissolving 10u moles $\pm$-L-FH$_4$ in 5 ml of 0.1M dithiothreitol with the addition of formaldehyde to give a final concentration of 20 mM and about 0.1 ml 1N NaOH). The reaction mixture contained a total of 25 umoles of phosphate. Incubation time was for 1 hour at 37° C. Under these conditions no phosphatase activity was present as shown by the background radioactivity present when the supernatant was incubated in the absence of 5,10-CH$_2$FH$_4$ (i.e., no conversion of $^3$H dUMP into $^3$H dUrd).

DHFR was partially purified from rat liver and assayed spectrophotometrically.

The results are tabulated below (Table 5). The I$_{50}$ was defined as the inhibitor concentration necessary to reduce the activity of TS by 50%. CB3717 was included as a reference compound so that the results could be expressed as an inverse relative potency (IRP) (I$_{50}$ test compound/I$_{50}$(CB3717).

TABLE 5

| Compound House number | TS I$_{50}$ (nM) | TS IRP | DHFR I$_{50}$ (uM) |
|---|---|---|---|
| CB3717 | *20.5 | — | 4,30** |
| CB3804 | 170.0 | 8.3 | 800 |
| CB3816 |  | 1136 |  |
| CB3824 |  | 53 |  |
| CB3822 |  | 26 |  |
| CB3826 |  | 56 |  |
| CB3866 | 1700 | 85 |  |

*Ki = 5 nM
(+)-5,10-CH$_2$FH$_4$ = 200 uM
**Repeat test with more pure material

The removal of the 2-amino group from the CB3717 structure resulted in a small decrease in potency for TS (8-fold). Much more striking loss of inhibitory activity was noted against DHFR.

Cell Culture

L1210 and L1210/C15 (overproduces TS 45-fold) were grown in continuous suspension culture in RPMI 1640 medium (20 mM HEPES) supplemented with 10% Horse Serum. Cells in the log phase of growth were diluted to about 5×10$^4$/ml and duplicate 5ml aliquots were added to 50 ml tissue culture flasks containing the appropriate additions (diluted in RPMI and sterilised by Millipore filtration). Cell counts after 48 hours of incubation were obtained by Coulter counting. The ID$_{50}$ was defined as that concentration of drug necessary to reduce the count to 50% control at 48 hours.

The ID$_{50}$ concentrations in L1210 and L1210/C15 cell culture are shown in Table 6. CB3717 was performed in parallel.

TABLE 6

| Compound House No. | ID$_{50}$ values (uM) L1210 | L1210/C15* |
|---|---|---|
| CB3717 | 6,7 | no inhibition at 100 uM |
| CB3804 | about 1, 0.8, 0.31 | no inhibition at 100 uM |
| CB3816 | 0.7 | |
| CB3824 | 1.1 | |
| CB3822 | 2.6 | |
| CB3826 | 1.7 | |

PTO for footnotes.
*These cells are not resistant to methotrexate or 5-CH$_3$-5,8-dideazaaminopterin (CB3703).
2 separate experiments
3 separate experiments CB3804 was about 7 times more potent than CB3717 against L1210 cells. The L1210/C15 cell line (acquired resistance to CB3717) was cross-resistant to CB3804. This strongly suggests that TS is the only locus of action involved in CB3804 cytotoxicity.

Reversal of the L1210 toxicity of CB3804 could be achieved by co-incubation with 10 uM thymidine (Table 7). Although reversal was complete in the presence of 5 uM CB 3804 incomplete reversal (75% of control growth) was noted at 50 uM. Again CB3717 (50 uM) was included as a control.

TABLE 7

| Compound (House No.) | Compound concentration uM | Cell count at 48 hours uM as % control |
|---|---|---|
| CB3717 | 50 | 103 |
| CB3804 | 5 | 98 |
| CB3804 | 50 | 75 |

Incorporation of $^3$H dUrd into acid-precipitable material

Figure 2:
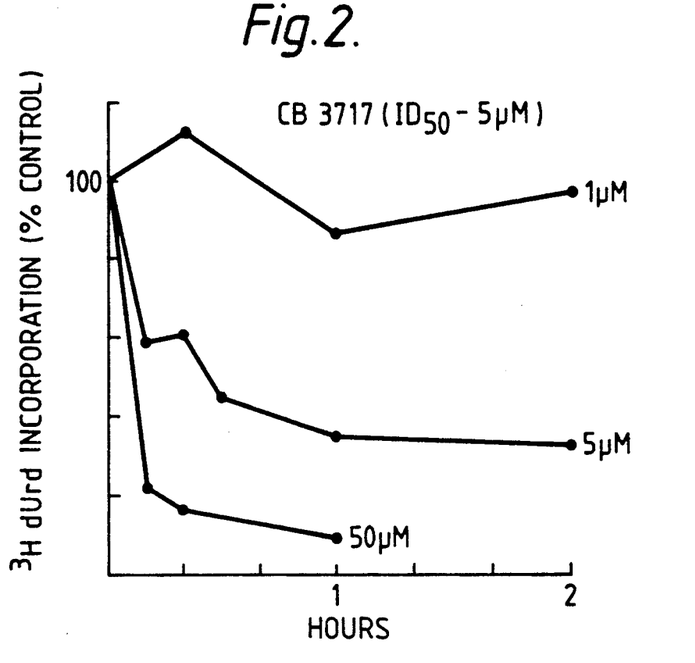
FIGS. 2 to 4 show the effect of various quinazoline antifolates on $^3$H dUrd incorporation into acid-precipitable material.
Figure 3:
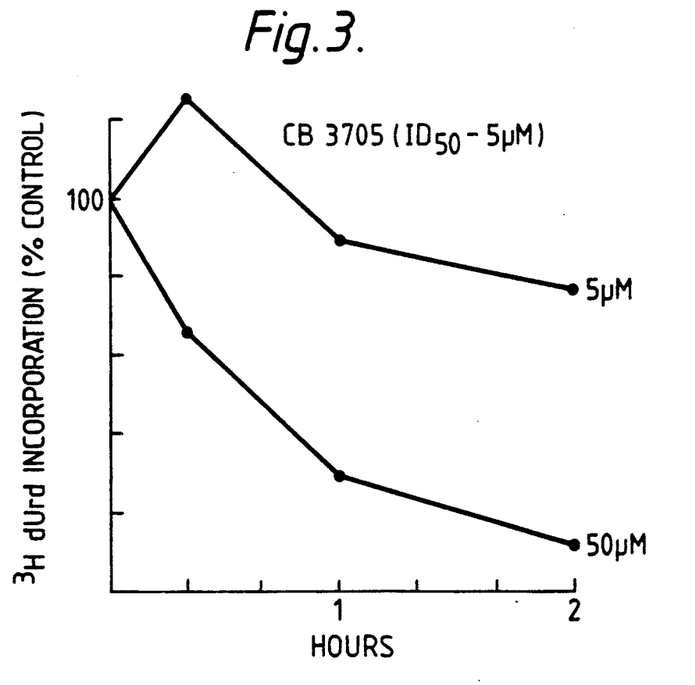
Figure 4:
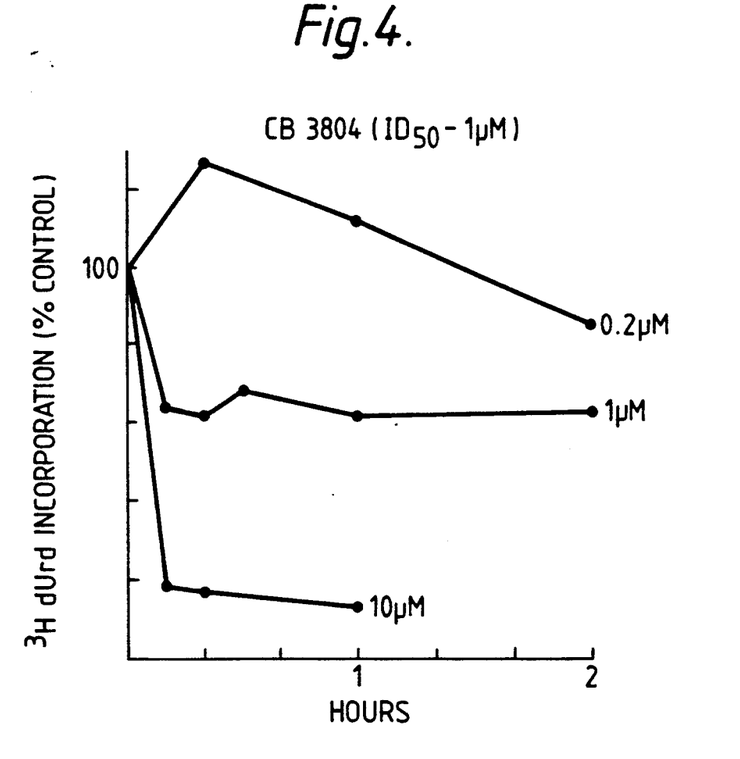

L1210 cells were used at a concentration of 10$^5$/ml. Incubation at 37° C. was in complete RPMI tissue culture medium plus or minus drugs for the lengths of time indicated on the graphs. After this time $^3$H dUrd was added at a concentration of 2 uCi/ml (about 0.2 uM). Three 1 ml aliquots were removed after 20 minutes, placed on ice and mixed with 1 ml of ice-cold phosphate buffered saline (PBS). Precipitation onto glass-fibre discs was performed by trichloroacetic acid washing followed by PBS. FIGS. 2, 3 and 4 compare the effects of various concentrations of CB3717, CB3705 (5,8-dideazafolic acid) and CB3804 on their ability to suppress the incorporation of $^3$H dUrd into acid-precipitable material. This is an indirect measurement of de novo thymidylate synthesis in whole cells. The "parent" compound (CB3705) did not significantly effect $^3$H dUrd incorporation over 2 hours at the ID$_{50}$ concentration (5 uM). Even 10 times this value did not produce rapid suppression (these results are similar to that found with MTX where cessation of de novo thymidylate synthesis is a secondary event resulting from DHFR inhibition). 50 uM CB3717 or 10 uM CB3804, reduced incorporation to <20% by about 10 minutes. These concentrations are 10 times the ID$_{50}$ values. The results suggest that CB3804 is very similar to CB3717 in that it results in a rapid inhibition of thymidylate synthesis but at a lower concentration (proportional to its ID$_{50}$).

Treatment of L1210 tumour-bearing mice

The L1210 tumour is carried routinely in DBA$_2$ mice at the Institute of Cancer Research (L1210/CBRI). For experiments 5×10$^4$ cells were implanted i.p. into male C57Bl×DBA$_2$F$_1$ hybrid mice 3 days prior to treatment. CB3804 and CB3717 was dissolved in 0.15M NaHCO$_3$ and adjusted to pH 9.5 before i.p. injection (daily ×5). The control group consisted of 9 mice and treated groups 6 or 7 mice.

Figure 5:
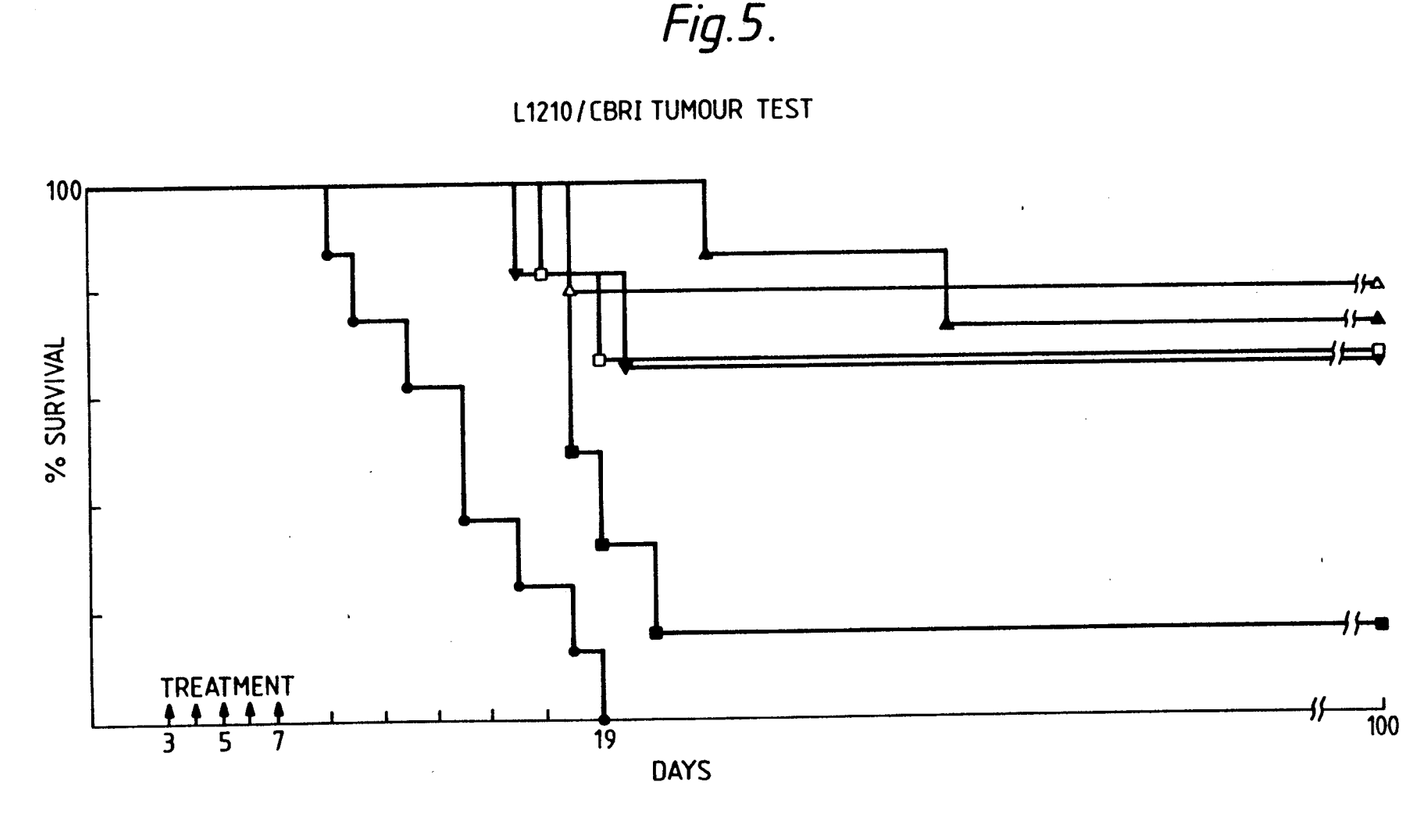
FIG. 5 illustrates anti-tumour activity of CB 3804.

The results are presented in FIG. 5 where ● Controls; ■ 25 mg/kg CB3804; □ 50 mg/kg CB3804; 100 mg/kg CB3804; ▼ 200 mg/lg CB3804; ▲ 50 mg/kg CB3717. CB3717 was included at one dose only (50 mg/kg), as 100 mg/kg (the optimal dose) has consistently given 80–100% "cures" in many previous experiments. In this test 50 mg/kg of CB3717 gave about 70% "cures" (survived >100 days). CB3804 administration resulted in about 80% "cures" at 100 mg/kg and about 65% at 50 mg/kg. There is no significant difference between any of the treatments with the exception of the 25 mg/kg dose of CB3804 which was much less effective. The highest dose (200 mg/kg) gave no obvious signs of toxicity and no weight loss occurred. This dose of CB3717 results in about 10% weight loss and death in about 50% of the animals (data not included).

Conclusions

CB3804 is a thymidylate synthase inhibitor and all the available evidence strongly suggests that this enzyme is its cytotoxic locus of action. A very significant reduction in inhibitory activity against DHFR was achieved and this may be important in determining good TS inhibition and cytotoxicity. The high level of DHFR in cells relative to TS (particularly in some MTX resistant mutants) may antagonise TS effects by sequestration of quinazoline-based inhibitors thereby reducing the level of "free" intracellular inhibitor available to bind to TS. In vivo, comparable anti-tumour activity with CB3717 was found. No signs of toxicity were apparent at the dose levels used (up to 200 mg/kg) which is in contrast to that normally observed with CB3717 at doses above 100 mg/kg.

TABLE 1

The Comparative Pharmacokinetics of CB3717 and CB3904 in The Mouse

| | Drug and Dose (mg/kg) | | | | |
|---|---|---|---|---|---|
| | CB3717 | | CB3804 | | |
| | 100 | 300 | 100 | 300 | 500 |
| Plasma quinazoline Conc. (uM) | | | | | |
| 3 h post-treatment | 134 ± 34 | 214 ± 55 | <5 | <5 | 5 |
| 6 h post-treatment | 59 ± 38 | 362 ± 32 | <5 | <5 | <5 |
| Liver quinazoline Level (% dose administered) | | | | | |
| 3 h post-treatment | 32 ± 4 | 22 ± 8 | <0.1 | <0.03 | <0.2 |
| 6 h post-treatment | 11 ± 2 | 14 ± 6 | <0.1 | <0.03 | <0.2 |
| Kidney quinazoline level (% dose administered) | | | | | |
| 3 h post-treatment | 13 ± 2 | 6 ± 1 | <0.1 | <0.03 | <0.1 |
| 6 h post-treatment | 20 ± 8 | 16 ± 1 | <0.1 | <0.03 | <0.1 |

Data are $\bar{x}$ ± S.D. n = 3

TABLE 2

Comparative Hepatotoxicty of CB3717 and CB3804 In The Mouse

| Plasma Alanine Transaminase Level (U/L) | Drug and Dose (mg/kg) | | | | |
|---|---|---|---|---|---|
| | CB3717 | | CB3804 | | |
| | 100 | 300 | 100 | 300 | 500 |
| 3 h post-treatment | 225 ± 146 | 86 ± 61 | 19 ± 3 | 10 ± 4 | 16 ± 3 |
| 6 h post-treatment | 273 ± 106 | 973 ± 178 | 10 ± 6 | 8 ± 3 | 16 ± 2 |

Data x̄ ± S.D. n = 3

TABLE 3

Urinary and Faecal Elimination of CB3804 and CB3717
in the Mouse Following 100 mg/kg i.p.
Time period 0-48 h

| | % of the dose administered excreted in the form given | |
|---|---|---|
| | CB3804 | CB3717 |
| Urinary excretion of the parent compound | 4 ± 1 | 15 ± 3 |
| Faecal excretion of the parent compound | 15 ± 13 | 26 ± 7 |
| Faecal excretion of metabolites | 27 ± 16* | 8 ± 3 |

*Metabolites identified as peaks not present in the pre-treatment faeces with 254/280 nm absorbance ratios consistent with CB3804.
Data are x̄ S.D. n = 3–6

TABLE 4

The Pharmacokinetics and Hepatotoxicity of C83717 and
CB3804 in Rats* 100 mg/kg given as a 1 h i.v. infusion

| | | CB3717 | | CB3804 | |
|---|---|---|---|---|---|
| Plasma levels (uM) | Mid inf | 412 | 447 | 275 | 258 |
| | End inf | 908 | 878 | 274 | 256 |
| | Inf + 1 h | 496 | 531 | 10 | 19 |
| | Inf + 2 h | 372 | 437 | <2 | <2 |
| | Inf + 3 h | 316 | 304 | <2 | <2 |
| | Inf + 4 h | 316 | 291 | <2 | <2 |
| Cumulative biliary excretion (% dose) | | 4 | 7 | 72 | 80 |
| Cumulative urinary excretion (% dose) | | 0.5 | 2.8 | 11 | 7 |
| Kidney level (% dose) | | 37 | 34 | <0.5 | <0.5 |
| Liver level (% dose) | | 9 | 9 | <0.5 | <0.5 |
| Peak Plasma Alanine Transaminase (% pre treatment) | | 1260 | 1400 | 57 | 143 |

*Each column refers to an individual rat

We claim:

1. A compound of formula I:

wherein
R is
1) hydrogen; or
2) an alkyl, alkenyl or alkynyl group of up to 6 carbon atoms;
n is 0; 1 or 2;
Z represents —CH=CH— [or —O—] or —S—;

each X independently represents halogeno, $C_1$–$C_4$ alkyl, $C_1$–$C_4$ alkoxy, nitro or trifluoromethyl; and
Y represents a group of formula:

a)   (L-aspartic acid residue)

b)   (L-glutamic acid residue)

or c)   (L-glutamyl-L-glutamic acid residue)

or d)   (L-alanine residue)

or e)   (L-2-amino-butyric acid residue)

or a pharmaceutically acceptable salt or ester thereof.

2. A compound according to claim 1 wherein n is 0 or 1.

3. A compound according to claim 1 wherein X is halogeno or $C_1$–$C_4$ alkyl

4. A compound according to claim 1 wherein X is fluoro.

5. A compound according to claim 4 wherein X is at the 2' position.

6. A compound according to claim 1 wherein Z represents —CH=CH—.

7. A compound according to claim 1 wherein Y is the residue of L-glutamic acid or a salt or ester thereof.

8. A compound according to claim 1 wherein R is an unsubstituted group of 1 to 4 carbon atoms.

9. A compound according to claim 6 wherein R is propargyl.

10. A compound according to claim 1 selected from N-(4-(N-((3,4-dihydro-4-oxo-6-quinazolinyl)methyl)-prop-2-ynylamino)benzoyl)-L-glutamic acid; N-(2-fluoro-4-(N-((3,4-dihydro-4-oxo-6-quinazolinyl)-methyl)prop-2-ynylamino)benzoyl)-L-glutamic acid; N-(4-(N-((3,4-dihydro-4-oxo-6-quinazolinyl)methyl)-methylamino)benzoyl)-L-glutamic acid; N-(4-(N-((3,4-dihydro-4-oxo-6-quinazolinyl)methyl)ethylamino)benzoyl)-L-glutamic acid; N-(4-(N-((3,4-dihydro-4-oxo-6-quinazolinyl)methyl)prop-2-enylamino)benzoyl)-L-glutamic acid and N-(4((((3,4-dihydro-4-oxo-6-quinazolinyl)methyl)amino)benzoyl-L-glutamic acid and salts and esters thereof.

11. A compound of formula (I) according to claim 1 in the form of a disodium salt or diethyl ester.

12. A pharmaceutical composition comprising a therapeutically effective amount of a compound of formula (I) as defined in claim 1 and a pharmaceutically acceptable carrier or diluent.

13. A composition according to claim 12 presented in a form suitable for parenteral, oral, topical or rectal administration.

14. A composition according to claim 13 in sterile injectable form.

* * * * *

UNITED STATES PATENT AND TRADEMARK OFFICE
CERTIFICATE OF CORRECTION

PATENT NO. : 5,236,927
DATED : August 17, 1993
INVENTOR(S) : JONES et al

It is certified that error appears in the above-indentified patent and that said Letters Patent is hereby corrected as shown below:

Column 23, last line, delete "[or -O]".

Column 24, lines 54-55, delete "N-(4((((3,4-dihydro-4-oxo-6-quinazolinyl)methyl)amino)benzoyl-L-glutamic acid" and replace by --N-(4-(((3,4-dihydro-4-oxo-6-quinazolinyl)methyl)amino)benzoyl) -L-glutamic acid--.

Signed and Sealed this

Seventeenth Day of May, 1994

Attest:

BRUCE LEHMAN

Attesting Officer     Commissioner of Patents and Trademarks